(12) United States Patent
Kumagai et al.

(10) Patent No.: US 7,601,734 B2
(45) Date of Patent: Oct. 13, 2009

(54) CYCLIC AMINE COMPOUND

(75) Inventors: Toshihito Kumagai, Tokyo (JP); Toshio Nakamura, Tokyo (JP); Yuri Amada, Tokyo (JP); Yoshinori Sekiguchi, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 169 days.

(21) Appl. No.: 11/578,169

(22) PCT Filed: Apr. 8, 2005

(86) PCT No.: PCT/JP2005/007278

§ 371 (c)(1),
(2), (4) Date: Oct. 11, 2006

(87) PCT Pub. No.: WO2005/100355

PCT Pub. Date: Oct. 27, 2005

(65) Prior Publication Data

US 2007/0244145 A1 Oct. 18, 2007

(30) Foreign Application Priority Data

Apr. 12, 2004 (JP) .............................. 2004-116599

(51) Int. Cl.
*A61K 31/44* (2006.01)
*A61P 25/18* (2006.01)
*A61P 25/24* (2006.01)

(52) U.S. Cl. ........................ 514/291; 514/292; 546/198; 546/199

(58) Field of Classification Search ........................ None
See application file for complete search history.

(56) References Cited

U.S. PATENT DOCUMENTS

| 4,672,117 A | 6/1987 | Abou-Gharbia et al. |
| 6,303,614 B1 | 10/2001 | Kennis et al. |
| 6,576,640 B1 * | 6/2003 | Kennis et al. ............... 514/291 |

FOREIGN PATENT DOCUMENTS

| EP | 0905136 A1 | 3/1999 |
| JP | 62-070374 A | 3/1987 |
| JP | 2001-515899 A | 9/2001 |
| WO | WO 98/45297 | * 10/1998 |

OTHER PUBLICATIONS

Vippagunta et al, "Crystalline Solids", Advanced Drug Delivery Reviews, vol. 48, 2001, pp. 3-26.*

Gavezzotti, "Are Crystal Structures Predictable?", Accounts of Chemical Research, vol. 27, 1994, pp. 309-314.*

Kennis et al.: New 2-substituted 1,2,3,4-tetrahydrobenzofuro[3,2-c]pyridine having highly active and potent central alpha2-antagonistic activity as potential antidepressant. Bioorg Med Chem Letters, 10:71-74, 2000.*

Magid Abou-Gharbia, et al, "Psychotropic Agents: Synthesis and Antipsychotic Activity of Substituted β-Carbolines", Journal of Medicinal Chemistry, vol. 30, No. 6, 1987, pp. 1100 to 1105.

Magid Abou-Charbia, et al, Antipsychotic Activity of Substituted γ-Carbolines, Journal of Medicinal Chemistry, vol. 30, No. 10, 1987, pp. 1818 to 1823.

Charles A. Harbert, et al, Neuroleptic Activity in 5-Aryltetrahydro-γ-Carbolines, Journal of Medicinal Chemistry, vol. 23, No. 6, 1980, pp. 635 to 643.

Magid Abou-Gharbia, et al., "Psychotropic Agents: Synthesis and Antipsychotic Activity of Substituted β-Carbolines", Journal of Medicinal Chemistry, 1987, pp. 1100-1105, vol. 30, No. 6.

Magid Abou-Charbia, et al., Antipsychotic Activity of Substituted γ-Carbolines, Journal of Medicinal Chemistry, 1987, pp. 1818-1823, vol. 30, No. 10.

Charles A. Harbert, et al., Neuroleptic Activity in 5-Aryltetrahydro-γ-carbolines, Journal of Medicinal Chemistry, 1980, pp. 635-643, vol. 23, No. 6.

International Search Report dated Jun. 7, 2005.

* cited by examiner

*Primary Examiner*—Brian-Yong S Kwon
*Assistant Examiner*—Bong-Sook Baek
(74) *Attorney, Agent, or Firm*—Sughrue Mion, PLLC

(57) ABSTRACT

An object of the present invention is to provide a cyclic amine compound which has a potent inhibitory effect on the binding of α2C-adrenoceptor and is useful in preventing and treating disorders attributable to α2C-adrenoceptor.

The above-described object is solved by the following cyclic amine compound, etc.,

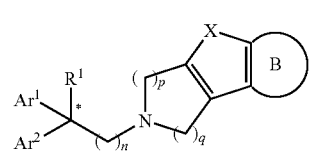

Formula (1)

wherein X is O, S, SO, $SO_2$ or $NR^2$, etc.; $R^1$ is a hydrogen atom, a cyano group, a carboxyl group, a $C_2$-$C_{13}$ alkoxycarbonyl group, a carbamoyl group, etc.; $Ar^1$ and $Ar^2$ are the same or different and each represent an aryl or heteroaryl group which may be substituted by 1 to 3 substituents and so on; ring B is a benzene ring may be substituted by 1 to 3 substituents and so on; n is an integer from 1 to 10; and p and q are the same or different and each represent an integer of 1 or 2.

8 Claims, No Drawings

CYCLIC AMINE COMPOUND

TECHNICAL FIELD

The present invention relates to a novel cyclic amine compound, a solvate thereof a pharmaceutically acceptable salt thereof and a pharmaceutical composition.

BACKGROUND ART

α2-Adrenoceptors are divided into three subtypes, i.e., α2A, α2B and α2C. Recently, experimental animals overexpressing or lacking an α2-adrenoceptor subtype gene have been created and tested. A clear anti-depressive effect was observed in animals lacking α2C gene, and an opposite effect was observed in animals overexpressing this gene. Thus, it has been demonstrated that α2C-adrenoceptor is closely associated with the development of depression (non-patent document 1).

Currently, neurotransmitter, such as serotonin or noradrenalin, uptake inhibitors are used widely as therapeutics for depression. For some of these inhibitors, it is suggested that their efficacy is exerted by the antagonism of α2-adrenoceptors (non-patent documents 2 and 3). α2-Adrenoceptor blockade increases the release of noradrenalin and serotonin, producing a therapeutic effect on depression. It is also suggested that the action of α2-adrenoceptors upon the cholinergic and dopaminergic nervous system produces a valuable effect on depression.

Among the α2-adrenoceptor antagonists of which application to anti-depressants have been examined, mirtazapine, mianserin, etc. are clinically used. However, since these drugs have various pharmacological effects, adverse effect occurs rather frequently. Considering these matters, it is believed that an α2C-adrenoceptor inhibitory compound will be useful as a therapeutic for stress-related mental disorders which is highly effective and has less adverse effect.

On the other hand, clozapine, which is an atypical antischizophrenic drug, is regarded as a therapeutic with the highest efficacy compared to conventional therapeutics. It is believed that the effect of clozapine results from the inhibition of activity of the mesolimbic dopaminergic nervous system by D2 receptor blockade. The excellent efficacy of clozapine is suggested to be attributable to the blocking of 5-TH2A receptor, D4 receptor or α2-adrenoceptor. With respect to other atypical antischizophrenic drugs such as risperidone, it is also reported that α2-adrenoceptor antagonism is involved in the curing of schizophrenia (non-patent document 4).

Further, it is reported based on an animal experiment that a remarkable release of dopamine from the medial prefrontal cortex was not observed with D2 receptor antagonist; that a remarkable release of dopamine was observed selectively in the medial prefrontal cortex when α2-adrenoceptor antagonist was jointly used; and that adverse effect on the extrapyramidal system was eliminated (non-patent document 5). It is also reported that α2-adrenoceptor antagonist is effective clinically in treating depression and schizophrenia (non-patent documents 6 and 7).

Initiation of catalepsy by D2 receptor blockade is inhibited by a compound with affinity for α2C-adrenoceptor (non-patent document 8). Further, since clozapine has high affinity for α2C subtype, it is believed that a compound which selectively blocks α2C-adrenoceptor among α2 subtypes can be a novel therapeutic for schizophrenia having remissive effect on negative symptoms and efficacy for refractory diseases.

A number of cyclic amine compounds have been reported to date (non-patent documents 9, 10, 11, 12 and 13; patent documents 1, 2, 3, 4 and 5). Non-patent documents 9 and 10 report actions on D2 receptor and 5-HT2A receptor and non-patent documents 11 and 12 report anti-amphetamine action, respectively. Nothing is described about action on α2-adrenoceptors in any of these documents. Non-patent document 13 and patent documents 1, 2, 3, 4 and 5 report about α2-adrenoceptor antagonism. With respect to a part of the compounds disclosed in patent documents 1 to 5, inhibitory actions on individual α2-adrenoceptor subtypes are described in non-patent document 13. However, α2C/α2A selectivity is hardly recognized in the compounds.

[patent document1] WO 98/45297
[patent document2] WO 00/20421
[patent document3] WO 00/20422
[patent document4] WO 00/20423
[patent document5] WO 00/37466
[non-patent document1] Sallinen et al, Mol. Psychiatry., (1999), 4(5), 443-452
[non-patent document2] Potter and Manji, Clin. Chem., (1994), 40(2), 279-287
[non-patent document3] Sussman and Stahl, Am. J. Med., (1996), 101(6A), 26S-36S
[non-patent document4] Hertel et al., Neuropsychopharmacology, (1997), 17(1), 44-55
[non-patent document5] Hertel et al., Science, (1999), 286 (5437), 105-107
[non-patent document6] Van Dorth, Acta. Psychiatry. Scand. Suppl., (1983), 302, 72-80
[non-patent document7] Litman et al., Br. J. Psychiatry., (1996), 168(5), 571-579
[non-patent document8] Kalkman et al., Br. J. Pharmacol., (1998), 124(7), 1550-1556
[non-patent document9] Abou-Gharbia et al., J. Med. Chem., (1987), 30, 1100-1105
[non-patent document10] Abou-Gharbia et al., J. Med. Chem., (1987), 30, 1818-1823
[non-patent document11] Harbert et al., J. Med. Chem., (1980), 23, 635-643
[non-patent document12] Harbert et al., Molecular Pharmacol., (1980), 17, 38-42
[non-patent document13] Kennis et al., Bioorg. Med. Chem. Lett., (2000), 10, 71-74

DISCLOSURE OF THE INVENTION

As described above, a novel cyclic amine compound which has a potent inhibitory effect on the binding of α2C-adrenoceptor and is useful in preventing and treating disorders attributable to α2C-adrenoceptor (such as depression, anxiety and schizophrenia) has not been provided yet. Development of such a cyclic amine compound is desired.

As a result of intensive and extensive researches toward the solution of the above problem, the present inventors have found that specific cyclic amine compounds have a potent and subtype-selective inhibitory activity against α2C-adrenoceptor. Thus, the present invention has been achieved. It is an object of the present invention to provide the cyclic amine compound described below, a solvate thereof or a pharmaceutically acceptable salt thereof, an α2C-adrenoceptor binding inhibitor, and a pharmaceutical composition for preventing and treating diseases attributable to α2C-adrenoceptor (such as depression, anxiety and schizophrenia).

(1) A cyclic amine compound represented by the following formula (I), a solvate thereof or a pharmaceutically acceptable salt thereof:

Formula (1)

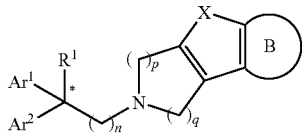

wherein X is O, S, SO, SO₂ or NR² (wherein R² is a hydrogen atom, a $C_1$-$C_{12}$ alkyl group, a $C_2$-$C_8$ alkanoyl group or a $C_2$-$C_{13}$ alkoxycarbonyl group);

R¹ is, when X is O, S, SO or SO₂, a hydrogen atom, a cyano group, a carboxyl group, a $C_2$-$C_{13}$ alkoxycarbonyl group, a carbamoyl group, a $C_2$-$C_{13}$ alkylaminocarbonyl group, a $C_3$-$C_{25}$ dialkylaminocarbonyl group, a $C_3$-$C_{13}$ cyclic aminocarbonyl group, a $C_1$-$C_{12}$ alkyl group, a $C_1$-$C_{12}$ alkoxy group, a $C_1$-$C_8$ alkylthio group, a $C_1$-$C_8$ alkylsulfinyl group, a $C_1$-$C_8$ alkylsulfonyl group, a $C_2$-$C_8$ alkanoyl group, a nitro group or a hydroxyl group; and when X is NR² (wherein R² is as defined above), R¹ is a cyano group, a carboxyl group, a $C_2$-$C_{13}$ alkoxycarbonyl group, a carbamoyl group, a $C_2$-$C_{13}$ alkylaminocarbonyl group, a $C_3$-$C_{25}$ dialkylaminocarbonyl group, a $C_3$-$C_{13}$ cyclic aminocarbonyl group, a $C_1$-$C_{12}$ alkyl group, a $C_1$-$C_{12}$ alkoxy group, a $C_1$-$C_8$ alkylthio group, a $C_1$-$C_8$ alkylsulfinyl group, a $C_1$-$C_8$ alkylsulfonyl group, a $C_2$-$C_8$ alkanoyl group, a nitro group or a hydroxyl group;

Ar¹ and Ar² are the same or different and each represent an aryl or heteroaryl group which may be substituted by 1 to 3 substituents selected arbitrarily from the group consisting of "halogen atoms, $C_1$-$C_{12}$ alkyl, $C_1$-$C_8$ haloalkyl, $C_7$-$C_{26}$ aralkyl, $C_2$-$C_8$ alkenyl, $C_2$-$C_8$ alkynyl, $C_1$-$C_{12}$ alkoxy, $C_1$-$C_8$ haloalkoxy, hydroxyl, $C_1$-$C_8$ alkylthio, $C_1$-$C_8$ alkylsulfinyl, $C_1$-$C_8$ alkylsulfonyl, $C_1$-$C_{12}$ alkylamino, $C_2$-$C_{24}$ dialkylamino, $C_2$-$C_{12}$ cyclic amino, amino, $C_2$-$C_{13}$ alkoxycarbonyl, carboxyl, $C_2$-$C_{13}$ alkylaminocarbonyl, $C_3$-$C_{25}$ dialkylaminocarbonyl, $C_3$-$C_{13}$ cyclic aminocarbonyl, carbamoyl, $C_2$-$C_8$ alkanoyl, cyano, nitro, phenyl and phenoxy groups"; or Ar¹ and Ar², together with adjacent carbon atoms attached thereto, form a group represented by any one of the following formulas (a) to (e):

(a)

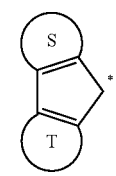

(b)

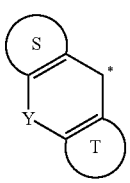

(c)

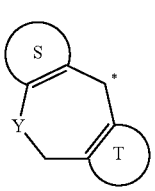

(d)

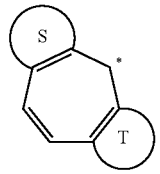

(e)

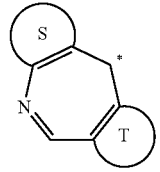

(wherein ring S and ring T are the same or different and each represent a benzene ring, a pyrrole ring, a furan ring, a thiophene ring, an imidazole ring, a pyrazole ring, an oxazole ring, an isoxazole ring, a thiazole ring, an isothiazole ring, a pyridine ring, a pyrimidine ring, a pyrazine ring or a pyridazine ring, each of which may be substituted by 1 to 3 substituents selected arbitrarily from the group consisting of "halogen atoms, $C_1$-$C_{12}$ alkyl, $C_1$-$C_8$ haloalkyl, $C_7$-$C_{26}$ aralkyl, $C_2$-$C_8$ alkenyl, $C_2$-$C_8$ alkynyl, $C_1$-$C_{12}$ alkoxy, $C_1$-$C_8$ haloalkoxy, hydroxyl, $C_1$-$C_8$ alkylthio, $C_1$-$C_8$ alkylsulfinyl, $C_1$-$C_8$ alkylsulfonyl, $C_1$-$C_{12}$ alkylamino, $C_2$-$C_{24}$ dialkylamino, $C_2$-$C_{12}$ cyclic amino, amino, $C_2$-$C_{13}$ alkoxycarbonyl, carboxyl, $C_2$-$C_{13}$ alkylaminocarbonyl, $C_3$-$C_{25}$ dialkylaminocarbonyl, $C_3$-$C_{13}$ cyclic aminocarbonyl, carbamoyl, $C_2$-$C_8$ alkanoyl, cyano, nitro, phenyl and phenoxy groups"; and Y is O, S, SO, SO₂ or NR³ (wherein R³ is a hydrogen atom, a $C_1$-$C_{12}$ alkyl group, a $C_2$-$C_8$ alkanoyl group or a $C_2$-$C_{13}$ alkoxycarbonyl group));

ring B is a benzene ring, a pyrrole ring, a furan ring, a thiophene ring, an imidazole ring, a pyrazole ring, an oxazole ring, an isoxazole ring, a thiazole ring, an isothiazole ring, a pyridine ring, a pyrimidine ring, a pyrazine ring or a pyridazine ring, each of which may be substituted by 1 to 3 substituents selected arbitrarily from the group consisting of "halogen atoms, $C_1$-$C_{12}$ alkyl, $C_1$-$C_8$ haloalkyl, $C_7$-$C_{26}$ aralkyl, $C_2$-$C_8$ alkenyl, $C_2$-$C_8$ alkynyl, $C_1$-$C_{12}$ alkoxy, $C_1$-$C_8$ haloalkoxy, hydroxyl, $C_1$-$C_8$ alkylthio, $C_1$-$C_9$ alkylsulfinyl, $C_1$-$C_8$ alkylsulfonyl, $C_1$-$C_{12}$ alkylamino, $C_2$-$C_{24}$ dialkylamino, $C_2$-$C_{12}$ cyclic amino, amino, $C_2$-$C_{13}$ alkoxycarbonyl, carboxyl, $C_2$-$C_{13}$ alkylaminocarbonyl, $C_3$-$C_{25}$ dialkylaminocarbonyl, $C_3$-$C_{13}$ cyclic aminocarbonyl, carbamoyl, $C_2$-$C_8$ alkanoyl, cyano, nitro, phenyl and phenoxy groups";

n is an integer from 1 to 10; and p and q are the same or different and each represent an integer of 1 or 2.

(2) The cyclic amine compound, solvate thereof or pharmaceutically acceptable salt thereof according to (1) above, wherein X is O, S, SO or SO₂;

R¹ is a hydrogen atom, a cyano group, a carboxyl group, a $C_2$-$C_{13}$ alkoxycarbonyl group, a carbamoyl group, a $C_2$-$C_{13}$ alkylaminocarbonyl group, a $C_3$-$C_{25}$ dialkylaminocarbonyl group, a $C_3$-$C_7$ cyclic aminocarbonyl group, a nitro group or a hydroxyl group;

Ar¹ and Ar² are the same or different and each represent a phenyl group, a naphthyl group, a furyl group, a thienyl group, a pyridyl group or an imidazolyl group, each of which may be substituted by 1 to 3 substituents selected arbitrarily from the group consisting of "halogen atoms, $C_1$-$C_{12}$ alkyl, $C_1$-$C_8$ haloalkyl, $C_1$-$C_{12}$ alkoxy, $C_1$-$C_8$ haloalkoxy, hydroxyl, $C_1$-$C_{12}$ alkylamino, $C_2$-$C_{24}$ dialkylamino, $C_2$-$C_{12}$ cyclic amino, amino, $C_2$-$C_{13}$ alkoxycarbonyl, carboxyl, $C_2$-$C_{13}$ alkylaminocarbonyl, $C_3$-$C_{25}$ dialkylaminocarbonyl, $C_3$-$C_{13}$ cyclic aminocarbonyl, carbamoyl, cyano, nitro, phenyl and phenoxy groups"; or $Ar^1$ and $Ar^2$, together with adjacent carbon atoms attached thereto, form a group represented by any one of the following formulas (f) to (j):

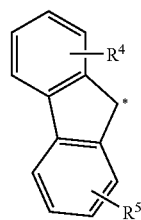
(f)

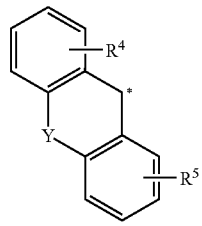
(g)

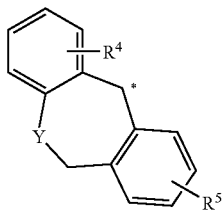
(h)

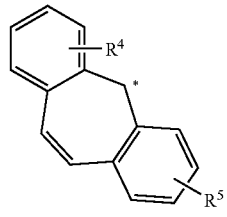
(i)

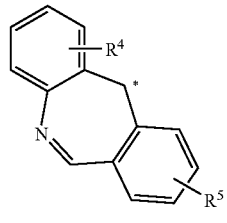
(j)

(wherein $R^4$ and $R^5$ are the same or different and each represent a hydrogen atom, a halogen atom, a $C_1$-$C_{12}$ alkyl group, a $C_1$-$C_8$ haloalkyl group, a $C_1$-$C_{12}$ alkoxy group, a $C_1$-$C_8$ haloalkoxy group, a hydroxyl group, a $C_1$-$C_{12}$ alkylamino group, a $C_2$-$C_{24}$ dialkylamino, a $C_2$-$C_{12}$ cyclic amino group, an amino group, a $C_2$-$C_{13}$ alkoxycarbonyl group, a carboxyl group, a $C_2$-$C_{13}$ alkylaminocarbonyl group, a $C_3$-$C_{25}$ dialkylaminocarbonyl group, a $C_3$-$C_{13}$ cyclic aminocarbonyl group, a carbamoyl group, a cyano group, a nitro group, a phenyl group or a phenoxy group; and Y is O, S, SO, $SO_2$ or $NR^3$ (wherein $R^3$ is a hydrogen atom or a $C_1$-$C_{12}$ alkyl group));

ring B is a benzene ring, a furan ring, a thiophene ring, a pyridine ring or an imidazole ring, each of which may be substituted by 1 to 3 substituents selected arbitrarily from the group consisting of "halogen atoms, $C_1$-$C_{12}$ alkyl, $C_1$-$C_8$ haloalkyl, $C_1$-$C_{12}$ alkoxy, $C_1$-$C_8$ haloalkoxy, hydroxyl, $C_1$-$C_{12}$ alkylamino, $C_2$-$C_{24}$ dialkylamino, $C_2$-$C_{12}$ cyclic amino, amino, $C_2$-$C_{13}$ alkoxycarbonyl, carboxyl, $C_2$-$C_{13}$ alkylaminocarbonyl, $C_3$-$C_{25}$ dialkylaminocarbonyl, $C_3$-$C_{13}$ cyclic aminocarbonyl, carbamoyl, cyano, nitro, phenyl and phenoxy groups";

n is an integer from 1 to 5; and p and q are different and each represent an integer of 1 or 2.

(3) The cyclic amine compound, solvate thereof or pharmaceutically acceptable salt thereof according to (1) above, wherein X is $NR^2$ (wherein $R^2$ is a hydrogen atom or a $C_1$-$C_{12}$ alkyl group);

$R^1$ is a cyano group, a carboxyl group, a $C_2$-$C_{13}$ alkoxycarbonyl group, a carbamoyl group, a $C_2$-$C_{13}$ alkylaminocarbonyl group, a $C_3$-$C_{25}$ dialkylaminocarbonyl group, a $C_3$-$C_7$ cyclic aminocarbonyl group, a nitro group or a hydroxyl group;

$Ar^1$ and $Ar^2$ are the same or different and each represent a phenyl group, a naphthyl group, a furyl group, a thienyl group, a pyridyl group or an imidazolyl group, each of which may be substituted by 1 to 3 substituents selected arbitrarily from the group consisting of "halogen atoms, $C_1$-$C_{12}$ alkyl, $C_1$-$C_8$ haloalkyl, $C_1$-$C_{12}$ alkoxy, $C_1$-$C_8$ haloalkoxy, hydroxyl, $C_1$-$C_{12}$ alkylamino, $C_2$-$C_{24}$ dialkylamino, $C_2$-$C_{12}$ cyclic amino, amino, $C_2$-$C_{13}$ alkoxycarbonyl, carboxyl, $C_2$-$C_{13}$ alkylaminocarbonyl, $C_3$-$C_{25}$ dialkylaminocarbonyl, $C_3$-$C_{13}$ cyclic aminocarbonyl, carbamoyl, cyano, nitro, phenyl and phenoxy groups"; or $Ar^1$ and $Ar^2$, together with adjacent carbon atoms attached thereto, form a group represented by any one of the following formulas (f) to (j):

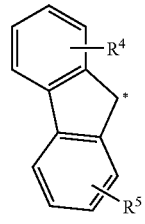
(f)

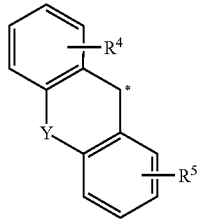
(g)

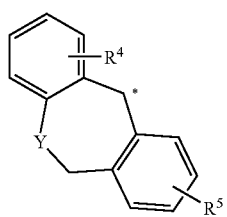
(h)

-continued

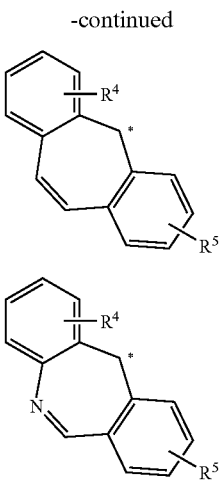

(wherein $R^4$ and $R^5$ are the same or different and each represent a hydrogen atom, a halogen atom, a $C_1$-$C_{12}$ alkyl group, a $C_1$-$C_8$ haloalkyl group, a $C_1$-$C_{12}$ alkoxy group, a $C_1$-$C_8$ haloalkoxy group, a hydroxyl group, a $C_1$-$C_2$ alkylamino group, a $C_2$-$C_{24}$ dialkylamino, a $C_2$-$C_{12}$ cyclic amino group, an amino group, a $C_2$-$C_{13}$ alkoxycarbonyl group, a carboxyl group, a $C_2$-$C_{13}$ alkylaminocarbonyl group, a $C_3$-$C_{25}$ dialkylaminocarbonyl group, a $C_3$-$C_{13}$ cyclic aminocarbonyl group, a carbamoyl group, a cyano group, a nitro group, a phenyl group or a phenoxy group; and Y is O, S, SO, $SO_2$ or $NR^3$ (wherein $R^3$ is a hydrogen atom or a $C_1$-$C_{12}$ alkyl group));

ring B is a benzene ring, a furan ring, a thiophene ring, a pyridine ring or an imidazole ring, each of which may be substituted by 1 to 3 substituents selected arbitrarily from the group consisting of "halogen atoms, $C_1$-$C_{12}$ alkyl, $C_1$-$C_8$ haloalkyl, $C_1$-$C_{12}$ alkoxy, $C_1$-$C_8$ haloalkoxy, hydroxyl, $C_1$-$C_{12}$ alkylamino, $C_2$-$C_{24}$ dialkylamino, $C_2$-$C_{12}$ cyclic amino, amino, $C_2$-$C_{13}$ alkoxycarbonyl, carboxyl, $C_2$-$C_{13}$ alkylaminocarbonyl, $C_3$-$C_{25}$ dialkylaminocarbonyl, $C_3$-$C_{13}$ cyclic aminocarbonyl, carbamoyl, cyano, nitro, phenyl and phenoxy groups";

n is an integer from 1 to 5; and p and q are different and each represent an integer of 1 or 2.

(4) The cyclic amine compound, solvate thereof or pharmaceutically acceptable salt thereof according to (1) above, wherein X is O or N;

$R^1$ is a hydrogen atom, a cyano group, a carboxyl group, a $C_1$-$C_6$ alkoxycarbonyl group or a carbamoyl group;

$Ar^1$ and $Ar^2$ are the same or different and each represent a phenyl group which may be substituted by halogen atom(s), $C_1$-$C_6$ alkyl group(s), $C_1$-$C_6$ alkoxy group(s), trifluoromethyl group(s) or trifluoromethoxy group(s); or $Ar^1$ and $Ar^2$, together with adjacent carbon atoms attached thereto, form a 9H-xanthene-9-yl group;

ring B is a benzene ring wherein one of its hydrogen atoms may be substituted by a halogen atom, a $C_1$-$C_6$ alkyl group, a $C_1$-$C_6$ alkoxy group, a trifluoromethyl group or a trifluoromethoxy group;

n is an integer from 2 to 4; and p and q are different and each represent an integer of 1 or 2.

(5) The cyclic amine compound, solvate thereof or pharmaceutically acceptable salt thereof according to (1) above, wherein X is $NR^2$ (wherein $R^2$ is a hydrogen atom, a methyl group or an ethyl group);

$R^1$ is a cyano group, a carboxyl group, a $C_1$-$C_6$ alkoxycarbonyl group or a carbamoyl group;

$Ar^1$ and $Ar^2$ are the same or different and each represent a phenyl group which may be substituted by halogen atom(s), $C_1$-$C_6$ alkyl group(s), $C_1$-$C_6$ alkoxy group(s), trifluoromethyl group(s) or trifluoromethoxy group(s);

ring B is a benzene ring wherein one of its hydrogen atoms may be substituted by a halogen atom, a $C_1$-$C_6$ alkyl group, a $C_1$-$C_6$ alkoxy group, a trifluoromethyl group or a trifluoromethoxy group;

n is an integer from 2 to 4; and p and q are different and each represent an integer of 1 or 2.

(6) An α2C-adrenoceptor binding inhibitor comprising the cyclic amine compound, solvate thereof or pharmaceutically acceptable salt thereof according to any one of (1) to (5) above.

(7) A pharmaceutical composition comprising the cyclic amine compound, solvate thereof or pharmaceutically acceptable salt thereof according to any one of (1) to (5) above and a pharmaceutically acceptable carrier.

(8) The pharmaceutical composition according to (7) above, which is used for preventing or treating depression, anxiety or schizophrenia.

According to the present invention, it is possible to provide a novel cyclic amine compound which has an inhibitory effect on the binding of α2C-adrenoceptor and is effective for disorders attributable to α2C-adrenoceptor (e.g., depression, anxiety or schizophrenia), a solvate of the compound or a pharmaceutically acceptable salt of the compound.

According to a preferred embodiment of the invention, it is possible to provide a novel cyclic amine compound with a high selectivity for α2C/α2A subtypes, a solvate thereof or a pharmaceutically acceptable salt thereof.

Further, according to a preferred embodiment of the invention, it is also possible to provide an α2C-adrenoceptor binding inhibitor, a prophylactic for diseases attributable to α2C-adrenoceptor (e.g., depression, anxiety or schizophrenia) and a therapeutic for these diseases.

BEST MODE FOR CARRYING OUT THE INVENTION

The Cyclic Amine Compound of the Present Invention

The cyclic amine compound of the present invention is represented by the following formula (I).

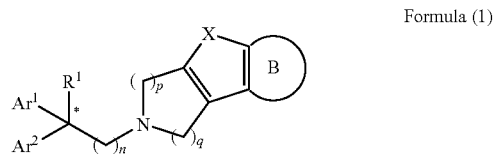

Formula (I)

In above formula (I), X is O, S, SO, $SO_2$ or $NR^2$ (wherein $R^2$ is a hydrogen atom, a $C_1$-$C_{12}$ alkyl group, a $C_2$-$C_8$ alkanoyl group or a $C_2$-$C_{13}$ alkoxycarbonyl group). Preferably, X is O, S, SO, $SO_2$ or $NR^2$ (wherein $R^2$ is a hydrogen atom or a $C_1$-$C_{12}$ alkyl group). More preferably, X is O, S or $NR^2$ (wherein $R^2$ is a hydrogen atom, a methyl group or an ethyl group).

When X is O, S, SO or $SO_2$, $R^1$ in above formula (I) is a hydrogen atom, a cyano group, a carboxyl group, a $C_2$-$C_{13}$ alkoxycarbonyl group, a carbamoyl group, a $C_2$-$C_{13}$ alkylaminocarbonyl group, a $C_3$-$C_{25}$ dialkylaminocarbonyl group, a $C_3$-$C_{13}$ cyclic aminocarbonyl group, a $C_1$-$C_{12}$ alkyl group, a $C_1$-$C_{12}$ alkoxy group, a $C_1$-$C_8$ alkylthio group, a $C_1$-$C_8$ alkylsulfinyl group, a $C_1$-$C_8$ alkylsulfonyl group, a $C_2$-$C_8$ alkanoyl group, a nitro group or a hydroxyl group. When X is O, S, SO or $SO_2$, $R^1$ is preferably a hydrogen atom, a cyano group, a carboxyl group, a $C_2$-$C_{13}$ alkoxycarbonyl group, a carbamoyl group, a $C_2$-$C_{13}$ alkylaminocarbonyl group, a $C_3$-$C_{25}$ dialkylaminocarbonyl group or a $C_3$-$C_{13}$ cyclic aminocarbonyl group.

When X is $NR^2$ (wherein $R^2$ is as defined above), $R^1$ in above formula (I) is a cyano group, a carboxyl group, a $C_2$-$C_{13}$ alkoxycarbonyl group, a carbamoyl group, a $C_2$-$C_{13}$ alkylaminocarbonyl group, a $C_3$-$C_{25}$ dialkylaminocarbonyl group, a $C_3$-$C_{13}$ cyclic aminocarbonyl group, a $C_1$-$C_{12}$ alkyl group, a $C_1$-$C_{12}$ alkoxy group, a $C_1$-$C_8$ alkylthio group, a $C_1$-$C_8$ alkylsulfinyl group, a $C_1$-$C_8$ alkylsulfonyl group, a $C_2$-$C_8$ alkanoyl group, a nitro group or a hydroxyl group. When X is $NR^2$ (wherein $R^2$ is as defined above), $R^1$ is preferably a cyano group, a carboxyl group, a $C_2$-$C_{13}$ alkoxycarbonyl group, a carbamoyl group, a $C_2$-$C_{13}$ alkylaminocarbonyl group, a $C_3$-$C_{25}$ dialkylaminocarbonyl group or a $C_3$-$C_{13}$ cyclic aminocarbonyl group.

$Ar^1$ and $Ar^2$ in above formula (I) may be the same or different. $Ar^1$ and $Ar^2$ each represent an aryl or heteroaryl group which may be substituted by 1 to 3 substituents selected arbitrarily from the group consisting of "halogen atoms, $C_1$-$C_{12}$ alkyl, $C_1$-$C_8$ haloalkyl, $C_7$-$C_{26}$ aralkyl, $C_2$-$C_8$ alkenyl, $C_2$-$C_8$ alkynyl, $C_1$-$C_{12}$ alkoxy, $C_1$-$C_8$ haloalkoxy, hydroxyl, $C_1$-$C_8$ alkylthio, $C_1$-$C_8$ alkylsulfinyl, $C_1$-$C_8$ alkylsulfonyl, $C_1$-$C_{12}$ alkylamino, $C_2$-$C_{24}$ dialkylamino, $C_2$-$C_{12}$ cyclic amino, amino, $C_2$-$C_{13}$ alkoxycarbonyl, carboxyl, $C_2$-$C_{13}$ alkylaminocarbonyl, $C_3$-$C_{25}$ dialkylaminocarbonyl, $C_3$-$C_{13}$ cyclic aminocarbonyl, carbamoyl, $C_2$-$C_8$ alkanoyl, cyano, nitro, phenyl and phenoxy groups". The number of substituents in the aryl or heteroaryl group in $Ar^1$ and $Ar^2$ is preferably 1 or 0.

Preferable substituents on the aryl or heteroaryl group in $Ar^1$ and $Ar^2$ are halogen atoms, $C_1$-$C_{12}$ alkyl, $C_1$-$C_8$ haloalkyl, $C_7$-$C_{26}$ aralkyl, $C_2$-$C_8$ alkenyl, $C_2$-$C_8$ alkynyl, $C_1$-$C_{12}$ alkoxy, $C_1$-$C_8$ haloalkoxy, amino, carboxyl, carbamoyl, cyano, nitro, phenyl or phenoxy groups.

Alternatively, $Ar^1$ and $Ar^2$, together with adjacent carbon atoms attached thereto, may form a group represented by any one of the following formulas (a) to (e). Among the groups represented by formulas (a) to (e), the group represented by formula (b) is preferable

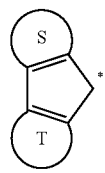

(a)

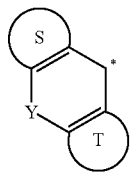

(b)

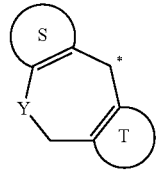

(c)

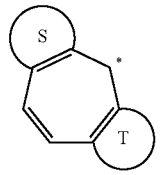

(d)

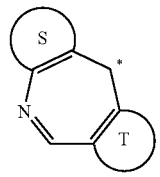

(e)

In above formulas (a) to (e), ring S and ring T may be the same or different. In above formulas (a) to (e), ring S and ring T each represent a benzene ring, a pyrrole ring, a furan ring, a thiophene ring, an imidazole ring, a pyrazole ring, an oxazole ring, an isoxazole ring, a thiazole ring, an isothiazole ring, a pyridine ring, a pyrimidine ring, a pyrazine ring or a pyridazine ring, each of which may be substituted by 1 to 3 substituents selected arbitrarily from the group consisting of "halogen atoms, $C_1$-$C_{12}$ alkyl, $C_1$-$C_8$ haloalkyl, $C_7$-$C_{26}$ aralkyl, $C_2$-$C_8$ alkenyl, $C_2$-$C_8$ alkynyl, $C_1$-$C_{12}$ alkoxy, $C_1$-$C_8$ haloalkoxy, hydroxyl, $C_1$-$C_8$ alkylthio, $C_1$-$C_8$ alkylsulfinyl, $C_1$-$C_8$ alkylsulfonyl, $C_1$-$C_{12}$ alkylamino, $C_2$-$C_{24}$ dialkylamino, $C_2$-$C_{12}$ cyclic amino, amino, $C_2$-$C_{13}$ alkoxycarbonyl, carboxyl, $C_2$-$C_{13}$ alkylaminocarbonyl, $C_3$-$C_{25}$ dialkylaminocarbonyl, $C_3$-$C_{13}$ cyclic aminocarbonyl, carbamoyl, $C_2$-$C_8$ alkanoyl, cyano, nitro, phenyl and phenoxy groups". Preferably, ring S and ring T in above formulas (a) to (e) each represent a mono-substituted ring or a non-substituted ring.

More preferably, ring S and ring T in above formulas (a) to (e) each represent a mono-substituted benzene ring or a non-substituted benzene ring. In this case, the groups represented by above formulas (a) to (e) correspond to the groups represented by formulas (f) to (j) described later, respectively.

Preferable substituents on ring S and ring T in formulas (a) to (e) are halogen atoms, $C_1$-$C_{12}$ alkyl, $C_1$-$C_8$ haloalkyl, amino, carboxyl, cyano, nitro, phenyl or phenoxy groups.

Y in formulas (b) and (c) is O, S, SO, $SO_2$ or $NR^3$ (wherein $R^3$ is a hydrogen atom, a $C_1$-$C_{12}$ alkyl group, a $C_2$-$C_8$ alkanoyl group or a $C_2$-$C_{13}$ alkoxycarbonyl group). In formulas (b) and (c), Y is preferably O, S, SO, $SO_2$ or $NR^3$ (wherein $R^3$ is a hydrogen atom or a $C_1$-$C_{12}$ alkyl group).

As described above, the groups represented by formulas (a) to (e) are preferably the groups represented by formulas (f) to (j), respectively. That is, $Ar^1$ and $Ar^2$ in formula (I), together with adjacent carbon atoms attached thereto, may form the group represented by any of the following formulas (f) to (j). Among the groups represented by formulas (f) to (j), the group represented by formula (g) is preferable.

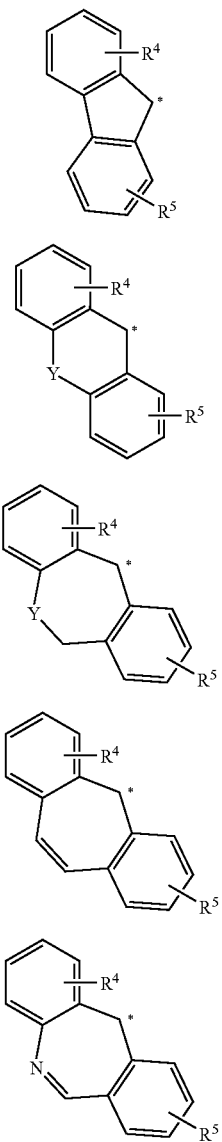

In formulas (f) to (j), $R^4$ and $R^5$ may be the same or different. In formulas (f) to (j), $R^4$ and $R^5$ each represent a hydrogen atom, a halogen atom, a $C_1$-$C_{12}$ alkyl group, a $C_1$-$C_8$ haloalkyl group, a $C_1$-$C_{12}$ alkoxy group, a $C_1$-$C_8$ haloalkoxy group, a hydroxyl group, a $C_1$-$C_{12}$ alkylamino group, a $C_2$-$C_{24}$ dialkylamino, a $C_1$-$C_{12}$ cyclic amino group, an amino group, a $C_2$-$C_{13}$ alkoxycarbonyl group, a carboxyl group, a $C_2$-$C_{13}$ alkylaminocarbonyl group, a $C_3$-$C_{25}$ dialkylaminocarbonyl group, a $C_3$-$C_{13}$ cyclic aminocarbonyl group, a carbamoyl group, a cyano group, a nitro group, a phenyl group or a phenoxy group. In formulas (f) to (j), $R^4$ and $R^5$ each represent preferably a hydrogen atom, a halogen atom, a $C_1$-$C_{12}$ alkyl group or a $C_1$-$C_8$ haloalkyl group, and more preferably a hydrogen atom or a halogen atom.

Y in formulas (f) to (j) is O, S, SO, $SO_2$ or $NR^3$ (wherein $R^3$ is a hydrogen atom or a $C_1$-$C_{12}$ alkyl group). Y is preferably O, S, SO or NH, and more preferably O.

(Ring B in Formula (1))

Ring B in formula (1) is a benzene ring, a pyrrole ring, a furan ring, a thiophene ring, an imidazole ring, a pyrazole ring, an oxazole ring, an isoxazole ring, a thiazole ring, an isothiazole ring, a pyridine ring, a pyrimidine ring, a pyrazine ring or a pyridazine ring, each of which may be substituted by 1 to 3 substituents selected arbitrarily from the group consisting of "halogen atoms, $C_1$-$C_{12}$ alkyl, $C_1$-$C_8$ haloalkyl, $C_7$-$C_{26}$ aralkyl, $C_2$-$C_8$ alkenyl, $C_2$-$C_8$ alkynyl, $C_1$-$C_{12}$ alkoxy, $C_1$-$C_8$ haloalkoxy, hydroxyl, $C_1$-$C_8$ alkylthio, $C_1$-$C_8$ alkylsulfinyl, $C_1$-$C_8$ alkylsulfonyl, $C_1$-$C_{12}$ alkylamino, $C_2$-$C_{24}$ dialkylamino, $C_2$-$C_{12}$ cyclic amino, amino, $C_2$-$C_{13}$ alkoxycarbonyl, carboxyl, $C_2$-$C_{13}$ alkylaminocarbonyl, $C_3$-$C_{25}$ dialkylaminocarbonyl, $C_3$-$C_{13}$ cyclic aminocarbonyl, carbamoyl, $C_2$-$C_8$ alkanoyl, cyano, nitro, phenyl and phenoxy groups".

The number of substituents in ring B in formula (1) is preferably 1 or 0. Ring B in formula (1) is preferably a benzene ring, a pyrrole ring, a furan ring, a pyridine ring, a pyrimidine ring or a pyrazine ring.

Preferable substituents on ring B in formula (1) are halogen atoms, $C_1$-$C_{12}$ alkyl, $C_1$-$C_8$ haloalkyl, $C_1$-$C_{12}$ alkoxy, $C_1$-$C_8$ haloalkoxy, hydroxyl, amino, carboxyl, carbamoyl, cyano, nitro, phenyl and phenoxy groups. More preferable substituents in ring B in formula (1) are halogen atoms, $C_1$-$C_{12}$ alkyl, $C_1$-$C_8$ haloalkyl, $C_1$-$C_{12}$ alkoxy and $C_1$-$C_8$ haloalkoxy groups.

n in formula (1) is an integer from 1 to 10. Preferably, n is an integer from 1 to 5; and more preferably, n is an integer from 2 to 4.

p and q in formula (1) may be the same or different and each represent an integer of 1 or 2. Preferably, p is 1 and q is 2; or p is 2 and q is 1.

(Description of Substituents, Etc.)

Hereinbelow, various substituents, etc. used in the present specification will be described.

The term "$C_1$-$C_{12}$ alkyl group" used herein means a straight-chain, branched or cyclic alkyl group having 1 to 12 carbon atoms, and examples thereof include methyl, ethyl, propyl, isopropyl, cyclopropyl, butyl, tert-butyl, pentyl, neopentyl, hexyl, cyclohexyl, heptyl, octyl, decyl and dodecyl groups. Among these, $C_1$-$C_6$ alkyl groups (e.g., methyl, ethyl and propyl groups) are preferable.

The term "$C_2$-$C_8$ alkanoyl group" used herein means a straight-chain, branched or cyclic alkanoyl group having 2 to 8 carbon atoms, and examples thereof include acetyl, propionyl, cyclopropanecarbonyl, butyryl, isobutyryl, pentyryl, isopentyryl, caproyl, enantyl, octylyl and cyclohexanecarbonyl groups. Among these, $C_2$-$C_4$ alkanoyl groups (e.g., acetyl and propionyl groups) are preferable.

The term "$C_2$-$C_{13}$ alkoxycarbonyl group" used herein means a carbonyl group substituted by a straight-chain, branched or cyclic alkoxy group having 1 to 12 carbon atoms, and examples thereof include methoxycarbonyl, ethoxycarbonyl, propoxycarbonyl, butoxycarbonyl, tert-butoxycarbonyl, pentyloxycarbonyl, hexyloxycarbonyl, octyloxycarbonyl, decyloxycarbonyl and dodecyloxycarbonyl groups. Among these, $C_2$-$C_7$ alkoxycarbonyl groups (e.g., methoxycarbonyl and ethoxycarbonyl groups) are preferable.

The term "$C_2$-$C_{13}$ alkylaminocarbonyl group" used herein means an aminocarbonyl group substituted by a straight-chain, branched or cyclic alkyl group having 1 to 12 carbon atoms, and examples thereof include methylaminocarbonyl, ethylaminocarbonyl, propylaminocarbonyl, isopropylaminocarbonyl, cyclopropylaminocarbonyl, butylaminocarbonyl, tert-butylaminocarbonyl, pentylaminocarbonyl, neopentylaminocarbonyl, hexylaminocarbonyl, cyclohexylaminocarbonyl, octylaminocarbonyl, decyl aminocarbonyl and dodecylaminocarbonyl groups. Among these, $C_2$-$C_7$ alkylaminocarbonyl groups are preferable.

The term "$C_3$-$C_{25}$ dialkylaminocarbonyl group" used herein means an aminocarbonyl group substituted by two (identical or different) straight-chain, branched or cyclic alkyl groups each having 1 to 12 carbon atoms, and examples thereof include dimethylaminocarbonyl, diethylaminocarbonyl, dipropylaminocarbonyl, diisopropylaminocarbonyl, dicyclopropylaminocarbonyl, butylpropylaminocarbonyl, heptylmethylaminocarbonyl, dioctylaminocarbonyl and didodecylaminocarbonyl groups. Among these, $C_3$-$C_{13}$ dialkylaminocarbonyl groups are preferable.

The term "$C_3$-$C_{13}$ cyclic aminocarbonyl group" used herein means a carbonyl group to which a cyclic amino group having 2 to 12 carbon atoms is attached, and examples thereof include 1-aziridylcarbonyl, 1-azetidylcarbonyl, 1-pyrrolidylcarbonyl, piperidinocarbonyl, 1-perhydroazepinylcarbonyl, 1-perhydroazosvlcarbonyl, 1-perhydroazonylcarbonyl, 1-imidazolidinylcarbonyl, 1-pyrazolidinylcarbonyl, 1-piperazinylcarbonyl, 3-oxazolidinylcarbonyl and morpholinocarbonyl groups. Among these, $C_3$-$C_7$ cyclic aminocarbonyl groups are preferable.

The term "$C_1$-$C_{12}$ alkoxy group" used herein means a straight-chain, branched or cyclic alkoxy group having 1 to 12 carbon atoms, and examples thereof include methoxy, ethoxy, propoxy, isopropoxy, cyclopropoxy, butoxy, tert-butoxy, pentyloxy, neopentyloxy, hexyloxy, cyclohexyloxy, heptyloxy, octyloxy, decyloxy and dodecyloxy groups. Among these, $C_1$-$C_6$ alkoxy groups are preferable.

The term "$C_1$-$C_8$ alkylthio group" used herein means a straight-chain, branched or cyclic alkylthio group having 1 to 8 carbon atoms, and examples thereof include methylthio, ethylthio, propylthio, isopropylthio, cyclopropylthio, butylthio, tert-butylthio, pentylthio, neopentylthio, hexylthio, cyclohexylthio and octylthio groups. Among these, $C_1$-$C_4$ alkylthio groups are preferable.

The term "$C_1$-$C_8$ alkylsulfinyl group" used herein means a sulfinyl group substituted by a straight-chain, branched or cyclic alkyl group having 1 to 8 carbon atoms, and examples thereof include methanesulfinyl, ethanesulfinyl, propanesulfinyl, isopropanesulfinyl, cyclopropanesulfinyl, butanesulfinyl, tert-butanesulfinyl, pentanesulfinyl, neopentanesulfinyl, hexanesulfinyl, cyclohexanesulfinyl and octanesulfinyl groups. Among these, $C_1$-$C_4$ alkylsulfinyl groups are preferable.

The term "$C_1$-$C_8$ alkylsulfonyl group" used herein means a sulfonyl group substituted by a straight-chain, branched or cyclic alkyl group having 1 to 8 carbon atoms, and examples thereof include methanesulfonyl, ethanesulfonyl, propanesulfonyl, isopropanesulfonyl, cyclopropanesulfonyl, butanesulfonyl, tert-butanesulfonyl, pentanesulfonyl, neopentanesulfonyl, hexanesulfonyl, cyclohexanesulfonyl and octanesulfonyl groups. Among these, $C_1$-$C_4$ alkylsulfonyl groups are preferable.

The term "halogen atom" used herein refers to a fluorine, chlorine, bromine or iodine atom. Among these, a fluorine, chlorine or bromine atom is preferable.

The term "$C_1$-$C_8$ haloalkyl group" used herein means a straight-chain, branched or cyclic alkyl group having 1 to 8 carbon atoms substituted by 1 to 3 halogen atoms, and examples thereof include trifluoromethyl, trichloromethyl, 2,2,2-trifluoroethyl, 4,4,4-trifluorobutyl, 3-chloropropyl and 4-bromobutyl groups. Among these, $C_1$-$C_4$ haloalkyl groups are preferable.

The term "$C_7$-$C_{26}$ aralkyl group" used herein means a straight-chain, branched or cyclic alkyl group having 1 to 8 carbon atoms substituted by 1 to 3 phenyl groups or pyridyl groups (these substituents may be the same or different), and examples thereof include benzyl, phenethyl, 4,4-diphenylbutyl, 2-picolyl, 3-picolyl, 4-picolyl and trityl groups. Among these, $C_7$-$C_{13}$ aralkyl groups are preferable.

The term "$C_2$-$C_8$ alkenyl group" used herein means a straight-chain, branched or cyclic alkenyl group having 2 to 8 carbon atoms, and examples thereof include vinyl, allyl, propenyl, isopropenyl, butenyl, cyclobutenyl, hexadienyl and octenyl groups. Among these, $C_2$-$C_4$ alkenyl groups are preferable.

The term "$C_2$-$C_8$ alkynyl group" used herein means a straight-chain, branched or cyclic alkynyl group having 2 to 8 carbon atoms, and examples thereof include ethynyl, propynyl, pentanediyl, hexynyl and octynyl groups. Among these, $C_2$-$C_4$ alkynyl groups are preferable.

The term "$C_1$-$C_8$ haloalkoxy group" used herein means a straight-chain, branched or cyclic alkoxy group having 1 to 8 carbon atoms substituted by, for example, 1 to 3 halogen atoms, and examples thereof include trifluoromethoxy, trichloromethoxy, 2,2,2-trifluoroethoxy, 4,4,4-trifluorobutoxy, 3-chloropropoxy and 4-bromobutoxy groups. Among these, $C_1$-$C_4$ haloalkoxy groups are preferable.

The term "$C_1$-$C_{12}$ alkylamino group" used herein means an amino group substituted by a straight-chain, branched or cyclic alkyl group having 1 to 12 carbon atoms, and examples thereof include methylamino, ethylamino, propylamino, isopropylamino, cyclopropylamino, butylamino, tert-butylamino, pentylamino, neopentylamino, hexylamino, cyclohexylamino, heptylamino, octylamino, decylamino and dodecylamino groups. Among these, $C_1$-$C_6$ alkylamino groups are preferable.

The term "$C_2$-$C_{24}$ dialkylamino group" used herein means an amino group substituted by two straight-chain, branched or cyclic alkyl groups (which are the same or different) having 1 to 12 carbon atoms, and examples thereof include dimethylamino, diethylamino, dipropylamino, diisopropylamino, dicyclopropylamino, butylpropylamino, heptylmethylamino, dioctylamino and didodecylamino groups. Among these, $C_2$-$C_{12}$ dialkylamino groups are preferable.

The term "$C_2$-$C_{12}$ cyclic amino group" used herein means a cyclic amino group having 2 to 12 carbon atoms, and examples thereof include 1-aziridyl, 1-azetidyl, 1-pyrrolidyl, piperidino, 1-perhydroazepinyl, 1-perhydroazosyl, 1-perhydroazonyl, 1-imidazolidinyl, 1-pyrazolidinyl, 1-piperazinyl, 3-oxazolidiny and morpholino groups. Among these, $C_2$-$C_6$ cyclic amino groups are preferable.

The term "aryl group" used herein means a group derived from an aromatic hydrocarbon ring by removing one hydrogen that is bonded to the ring, and examples thereof include phenyl, tolyl and naphthyl groups. Among these, phenyl and naphthyl groups are preferable.

The term "heteroaryl group" used herein means a monocyclic or condensed aromatic ring having in its ring 1 to 4 atoms selected arbitrarily from oxygen, sulfur and nitrogen atoms, and examples thereof include pyrolyl, furyl, thienyl, imidazolyl, pyrazolyl, oxazolyl, isooxazolyl, thiazolyl, isothiazolyl, 1,2,3-triazolyl, 1,2,4-triazolyl, 1,2,3,4-tetrazolyl, pyridyl, pyrimidinyl, pyrazinyl, pyridazinyl, indazolyl, benzofuryl, benzothienyl, benzoimidazolyl, benzoxazolyl, benzothiazolyl, quinolyl, isoquinolyl, quinoxalinyl, quinazolinyl, phthalazinyl and naphthyridinyl groups.

(Specific Examples of the Cyclic Amine Compound of the Present Invention)

Specific examples of the cyclic amine compound of the present invention include, but are not limited to, the following compounds.

Compound 1:
Methyl 5-(3,4-dihydro[1]benzofuro[3,2-c]pyridine-2(1H)-yl)-2,2-bis(4-fluorophenyl)pentanoate;
Compound 2:
5-(3,4-dihydro[1]benzofuro[3,2-c]pyridine-2(1H)-yl)-2,2-bis(4-fluorophenyl)pentanoic acid;
Compound 3:
5-(3,4-dihydro[1]benzofuro[3,2-c]pyridine-2(1H)-yl)-2,2-bis(4-fluorophenyl)pentanoic acid amide;
Compound 4:
5-(3,4-dihydro[1]benzofuro[3,2-c]pyridine-2(1H)-yl)-2,2-bis(4-fluorophenyl)pentanenitrile;
Compound 5:
5-(3,4-dihydro[1]benzofuro[3,2-c]pyridine-2(1H)-yl)-2,2-diphenylpentanenitrile;
Compound 6:
5-(3,4-dihydro-[1]-benzofuro[2,3-C]pyridine-2(1H)-yl)-2,2-diphenyl-pentanenitrile;
Compound 7:
5-(3,4-dihydro-[1]-benzothieno[3,2-C]pyridine-2(1H)-yl)-2,2-diphenyl-pentanenitrile;
Compound 8:
2,2-diphenyl-5-(1,3,4,5-tetrahydro-2H-pyrido[4,3-b]indole-2-yl)-pentanenitrile;
Compound 9:
5-(5-methyl-1,3,4,5-tetrahydro-2H-pyrido[4,3-b]indole-2-yl)-2,2-diphenyl-pentanenitrile;
Compound 10:
5-(8-fluoro-3,4-dihydro-[1]-benzofuro[3,2-C]pyridine-2 (1H)-yl)-2,2-diphenyl-pentanenitrile;
Compound 11:
5-(8-chloro-3,4-dihydro-[1]-benzofuro[3,2-C]pyridine-2 (1H)-yl)-2,2-diphenyl-pentanenitrile;
Compound 12:
5-(8-methyl-3,4-dihydro-[1]-benzofuro[3,2-C]pyridine-2 (1H)-yl)-2,2-diphenyl-pentanenitrile;
Compound 13:
5-(8-methoxy-3,4-dihydro-[1]-benzofuro[3,2-C]pyridine-2 (1H)-yl)-2,2-diphenyl-pentanenitrile;
Compound 14:
2,2-diphenyl-5-(8-trifluoromethoxy-3,4-dihydro-[1]-benzofuro[3,2-C]pyridine-2(1H)-yl)-pentanenitrile;
Compound 15:
2-(4,4-diphenylbutyl)-1,2,3,4-tetrahydro-[1]-benzofuro[3,2-C]pyridine;
Compound 16:
9-[3-(3,4-dihydro-[1]-benzofuro[3,2-C]pyridine-2(1H)-yl)-propyl]-9H-xanthene-carbonitrile
Compound 17:
4-(3,4-dihydro-[1]-benzofuro[3,2-C]pyridine-2(1H)-yl)-2,2-diphenyl-butyronitrile;
Compound 18:
6-(3,4-dihydro-[1]-benzofuro[3,2-C]pyridine-2(1H)-yl)-2,2-diphenyl-hexanenitrile.

The cyclic amine compound of the invention may be a solvate thereof or a pharmaceutically acceptable salt thereof. Hereinafter, the term "the compound of the invention" used herein sometimes includes the cyclic amine compound of the invention, solvates thereof and pharmaceutically acceptable salts thereof.

In the present specification, examples of the solvate include pharmaceutically acceptable solvates such as hydrates. When exposed to the air or being recrystallized, the cyclic amine compound of the invention may absorb moisture. As a result, the compound may be covered with adsorbed water or become a hydrate. The solvate of the cyclic amine compound of the invention also include such a hydrate.

In the present specification, examples of the pharmaceutically acceptable salt may include acid addition salts such as mineral acid salts (e.g., hydrochlorides, hydrobromates, hydroiodates, sulfates, phosphates or nitrates), sulfonic acid salts (e.g., methanesulfonates, ethanesulfonates, benzenesulfonates or p-toluenesulfonates) and organic acid salts (e.g., oxalates, tartrates, citrates, maleates, succinates, acetates, benzoates, mandelates, ascorbates, lactates, gluconates or maleates); amino acid salts such as glycine salts, lysine salts, arginine salts, ornithine salts, glutamates or aspartates; inorganic salts (e.g., lithium salts, sodium salts, potassium salts, calcium salts or magnesium salts) or ammonium salts; and salts with an organic base such as triethylamine salts, diisopropylamine salts or cyclohexylamine salts. Among these, hydrochlorides, hydrobromates, phosphates, methanesulfonates, p-toluenesulfonates, oxalates, tartrates, citrates, acetates, lactates, glutamates, aspartates, sodium salts, potassium salts, ammonium salts or triethylamine salts are suitable. Preferably, sodium salts, hydrochlorides or sulfates are used; more preferably, hydrochlorides are used. It should be noted that the compound of the invention also includes such a compound that is converted into the compound of the invention in the body through metabolism, so called pro-drug.

The cyclic amine compound of the invention may have isomers, such as cis- and trans-isomers. The cyclic amine compound of the invention includes such isomers, as well as a mixture of the cyclic amine compound and such isomers contained at any ratios. The cyclic amine compound may have an asymmetric center. In that case, compounds of various optical isomerisms or configurations may exist. Therefore, the compound of the invention may exist as different optically active substances, (+) and (−), and racemic modifications or (±) mixtures. When the compound of the invention has two or more asymmetric centers, diastereomers derived from individual optical isomerisms may also exist. The cyclic amine compound of the invention includes all of these types at any ratios. Diastereomers may be resolved by methods well-known to those skilled in the art, such as fractional crystallization; and optically active substances may be obtained by organic chemical techniques well-known for that purpose.

(Methods for Producing the Compound of the Invention)

The compound of the invention may be produced by known organic chemical techniques. For example, the compound of the invention may be produced according to any of the methods shown in the following reaction schemes.

In the reaction schemes 1 to 5 described below, $Ar^1$, $Ar^2$, n, X, p, q and ring B are as defined above; $R^1$ is a $C_1$-$C_{12}$ alkyl group, a $C_1$-$C_{12}$ alkoxy group, an amino group, a $C_1$-$C_{12}$ alkylamino group, a $C_2$-$C_{24}$ dialkylamino group or a $C_2$-$C_{12}$ cyclic amino group; $R^7$ is a conventional alcohol protective group; and Z is a halogen atom (such as chlorine, bromine or iodine atom) or a leaving group (such as methanesulfonyloxy, benzenesulfonyloxy or trifluoromethanesulfonyloxy group).

(Reaction Scheme 1)

Hereinbelow, a method for producing the compound of the invention as shown in the following reaction scheme 1 will be described. This production process is a process for producing compound (8) of the invention from compound (2).

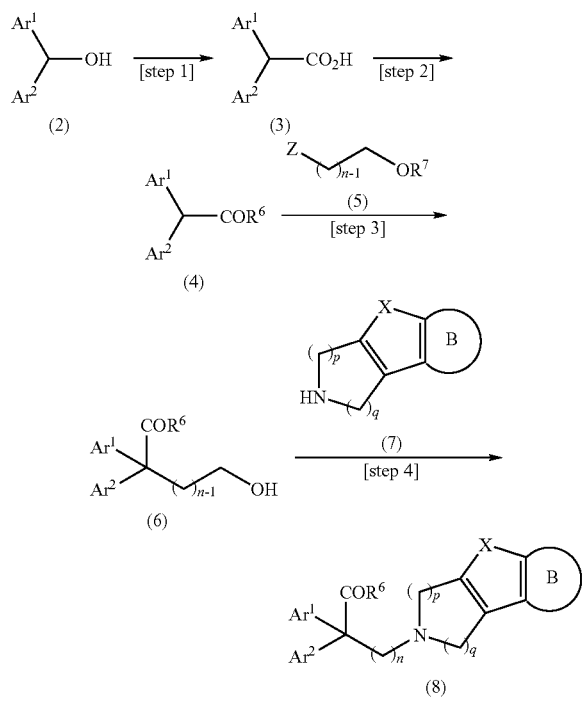

(Step 1)

Step 1 is a step to substitute the hydroxyl group of compound (2) with a carboxyl group to thereby obtain compound (3). Compound (2) may be converted into compound (3) according to, for example, by the method disclosed in Takahashi Y et al. Chemistry letters, 1985, 1733-1734. Compound (2) is a known compound or a compound which can be easily synthesized from a known compound.

(Step 2)

Step 2 is a step to esterify or amidate compound (3) to thereby obtain compound (4). As to the method of esterification in step 2, conditions employed in conventional esterification of carboxylic acid may be used. For example, the esterification may be achieved according to the method described in T. W. Greene and P. G. M. Wuts, Protective Groups in Organic Synthesis. As to the method of amidation in step 2, conditions employed in conventional amidation of carboxylic acid may be used. For example, a method in which carboxylic acid is converted into a carboxylic acid halide such as carboxylic acid chloride or carboxylic acid bromide, and then reacted with amine; a method in which a mixed acid anhydride obtained from carboxylic acid and chlorcarbonate or the like is reacted with amine; a method in which carboxylic acid is converted into an active ester such as 1-benzotriazolyl ester or succinimidyl ester, and then reacted with amine; or a method in which carboxylic acid is reacted with amine in the presence of a dehydration condensing agent may be used. All of these reactions may be carried out in an inert solvent in the presence or absence of a base.

When a dehydration condensing agent is used in step 2, examples thereof include 3-(3-dimethylaminopropyl)-1-ethylcarbodiimide hydrochloride, dicyclohexylcarbodiimide, diphenylphosphoryl azide and carbonyldiimidazole. If necessary, an activator such as 1-hydroxybenzotriazole or hydroxysuccinimide may be used.

When a base is used in step 2, examples thereof include organic amines such as pyridine, triethylamine or diisopropylethylamine; and inorganic bases such as potassium carbonate, sodium hydrogencarbonate or sodium hydroxide.

Examples of the inert solvent used in step 2 include alcohols such as methanol ethanol or isopropanol; ethers such as diethyl ether, tetrahydrofuran or 1,4-dioxane; aromatic hydrocarbons such as toluene or benzene; halogenated hydrocarbons such as chloroform or dichloromethane; amides such as dimethylformamide or N-methyl-2-pyrrolidon; dimethyl sulfoxide; acetonitrile; water and a mixture thereof (Step 3)

Step 3 is a step to react compound (4) with compound (5) in an inert solvent in the presence of a base, and then to remove protective group $R^7$ to thereby obtain compound (6). Compound (5) is a known compound or a compound which can be easily synthesized from a known compound. $R^7$ in compound (5) is a conventional alcohol protective group, and examples thereof include tetrahydropyranyl, methoxymethyl, benzyl, paramethoxybenzyl, trityl, trimethylsilyl, t-butyldimethylsilyl, acetyl and benzoyl groups.

Examples of the base used in step 3 include inorganic bases such as potassium carbonate, sodium carbonate, sodium hydride or potassium hydride; metal amides such as sodium amide, lithium bis(trimethylsilylamide) or lithium diisopropylamide; alcoholates such as sodium methoxide or potassium t-butoxide; and organic bases such as triethylamine or pyridine.

Examples of the inert solvent used in step 3 include alcohols such as methanol, ethanol or isopropanol; ethers such as diethyl ether, tetrahydrofuran or 1,4-dioxane; aromatic hydrocarbons such as toluene or benzene; halogenated hydrocarbons such as chloroform or dichloromethane; amides such as dimethylformamide or N-methyl-2-pyrrolidon; dimethyl sulfoxide; acetonitrile; water and a mixture thereof.

The deprotection in step 3 may be performed by a well-known method in the art of organic synthetic chemistry. For example, the method described in T. W. Greene and P. G. M. Wuts, Protective Groups in Organic Synthesis or John Wiley and Sons: J. F. W. McOmis, Protective Groups in Organic Chemistry, Plenum Press may be used.

(Step 4)

Step 4 is a step to carry out a condensation reaction between compound (6) and compound (7) to thereby obtain compound (8) of the invention. Compound 7 is a known compound or a compound which can be easily synthesized from a known compound according to, for example, such methods described in Cattanach et al., J. Chem. Soc. (C), (1971), 53-60; Capps et al., J. Am. Chem. Soc., (1953), 75, 697-699; Jaen et al. J., Heterocycl. Chem., (1987), 24, 1317-1319; and Campaigne et al., J. Heterocycl. Chem., (1979), 16(7), 1321-1324.

As to the condensation reaction in step 4, a method may be used, for example, in which compound (6) is reacted with a halogenating agent or sulfonylating agent in an inert solvent in the presence or absence of a base to thereby convert the hydroxyl group into an appropriate leaving group, and then a condensation reaction is performed in an inert solvent in the presence or absence of a base. If necessary, sodium bromide, potassium iodide, or the like may be added to the reaction.

When a halogenating agent is used in step 4, examples thereof include thionyl chloride, thionyl bromide, phosphoryl chloride, phosphorus pentachloride and carbon tetrabromide-triphenylphosphine.

When a sulfonylating agent is used in step 4, examples thereof include methanesulfonyl chloride, benzenesulfonyl chloride, trifluoromethanesulfonic anhydride and N-phenyl-bis(trifluoromethanesulfonimide).

When a base is used in step 4, examples thereof include organic amines such as pyridine or triethylamine; and inorganic bases such as potassium carbonate, sodium hydrogencarbonate or sodium hydroxide.

Example of the inert solvent used in step 4 include alcohols such as methanol, ethanol or isopropanol; ethers such as diethyl ether, tetrahydrofuran or 1,4-dioxane; aromatic hydrocarbons such as toluene or benzene; halogenated hydrocarbons such as chloroform or dichloromethane; amides such as dimethylformamide or N-methyl-2-pyrrolidon; dimethyl sulfoxide; acetonitrile; water and a mixture thereof Another Embodiment of Step 4-1

Alternatively, compound (8) may also be obtained by reacting compound (6) with an organic phosphorus compound (such as triphenylphosphine or tributylphosphine) and diethyl azobiscarboxylate, di-t-butyl azobiscarboxylate or the like in an inert solvent. Examples of the inert solvent include ethers such as diethyl ether, tetrahydrofuran or 1,4-dioxane; aromatic hydrocarbons such as toluene or benzene; halogenated hydrocarbons such as chloroform or dichloromethane; amides such as dimethylformamide or N-methyl-2-pyrrolidon; dimethyl sulfoxide; acetonitrile and a mixture thereof Another Embodiment of Step 4-2

Alternatively, compound 8) may also be obtained by oxidizing the hydroxyl group of compound (6) in an inert solvent to convert it into aldehyde and then reacting the resultant compound (6) with a reducing agent in an inert solvent in the presence or absence of an acid. The oxidation may be performed by a conventional method for oxidizing alcohol into aldehyde, e.g., a method using dimethyl sulfoxide and an activator (such as oxalyl chloride, N-chlorosuccinimide or dichlorohexylcarbodiimide); a method using tetra-n-propylammonium perruthenate (VII) and N-methylmorpholine oxide; or a method using periodic acids such as Dess-Martin reagent (1,1,1-triacetoxy-1,1-dihydro-1,2-benziodoxol-3-(1H)-one). For example, the oxidation may be performed according to the method described in S. D. Burke and R. L. Danheiser, Oxidizing and Reducing Agents. Examples of the acid used in this step include inorganic acids such as hydrochloric acid, hydrobromic acid, sulfuric acid, nitric acid or phosphoric acid; and organic acids such as p-toluenesulfonic acid, methanesulfonic acid, trifluoroacetic acid, formic acid or acetic acid. Examples of the reducing agent used in this step include boron type reducing agents such as sodium borohydride, sodium cyanoborohydride, sodium triacetoxyborohydride or lithium borohydride. Examples of the inert solvent used in this step include ethers such as diethyl ether, tetrahydrofuran or 1,4-dioxane; aromatic hydrocarbons such as toluene or benzene; halogenated hydrocarbons such as chloroform or dichloromethane; amides such as dimethylformamide or N-methyl-2-pyrrolidon; dimethyl sulfoxide; acetonitrile and a mixture thereof (Conversion of the Substituent of the Compound of the Invention—1)

By converting the substituent of a compound of the invention by a known method, it is possible to obtain another compound of the invention. For example, when $R^1$ in formula (I) is an alkoxycarbonyl group in a compound of the invention, it is possible to obtain another compound of the invention in which $R^1$ in formula (1) is a carboxyl group by converting the alkoxycarbonyl group into a carboxyl group by a known method.

For conversion of the alkoxycarbonyl group in $R^1$ in formula (1) into a carboxyl group, a compound of the invention in which $R^1$ in formula (1) is an alkoxycarbonyl group may be hydrolyzed with an acid or a base. Examples of the acid used in the hydrolysis include inorganic acids such as hydrochloric acid, hydrobromic acid, dilute sulfuric acid, concentrated sulfuric acid, nitric acid or phosphoric acid; and organic acids such as trifluoroacetic acid or trifluoromethanesulfonic acid. Examples of the base used in the hydrolysis include inorganic bases such as sodium hydroxide or potassium hydroxide; and organic bases such as t-butoxypotassium.

(Conversion of the Substituent of the Compound of the Invention—2)

Further, when $R^1$ in formula (1) is a carboxyl group in a compound of the invention, it is possible to obtain another compound of the invention in which $R^1$ in formula (1) is a carbamoyl, alkylaminocarbonyl, dialkylaminocarbonyl or cyclic aminocarbonyl group by converting the carboxyl group into a carbamoyl, alkylaminocarbonyl, dialkylaminocarbonyl or cyclic aminocarbonyl group by a known method.

For conversion of the carboxyl group in $R^1$ in formula (1) into a carbamoyl, alkylaminocarbonyl, dialkylaminocarbonyl or cyclic aminocarbonyl group, a compound of the invention in which $R^1$ in formula (1) is a carboxyl group may be amidated. As a method of the amidation, a conventional method for amidating carboxylic acid may be used; thus, the method described in step 2 may be used.

(Reaction Scheme 2)

Hereinbelow, a method for producing the compound of the invention as shown in the following reaction scheme 2 will be described. This production process is a process for producing compound (10) of the invention by converting the carbamoyl group in compound (9) of the invention into a cyano group.

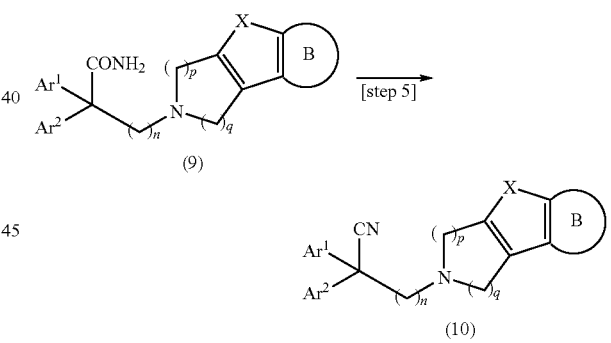

(Step 5)

Briefly, it is possible to obtain compound (10) of the invention by reacting compound (9) with a dehydrating agent in an inert solvent in the presence or absence of a base.

When a base is used in step 5, examples thereof include organic amines such as pyridine, triethylamine or diisopropylethylamine; and inorganic bases such as potassium carbonate or sodium hydrogencarbonate.

Examples of the dehydrating agent used in step 5 include trifluoroacetic anhydride, trifluoromethanesulfonic anhydride, benzoic anhydride, thionyl chloride, phosphoryl chloride or phosphorus pentaoxide.

Examples of the inert solvent used in step 5 include ethers such as diethyl ether, tetrahydrofuran or 1,4-dioxane; aromatic hydrocarbons such as toluene or benzene; halogenated hydrocarbons such as chloroform or dichloromethane;

amides such as dimethylformamide or N-methyl-2-pyrrolidon; dimethyl sulfoxide; acetonitrile and a mixture thereof (Reaction Scheme 3)

Hereinbelow, a method for producing the compound of the invention as shown in the following reaction scheme 3 will be described. This production process is a process for producing compound (10) of the invention from compound (2) or compound (4).

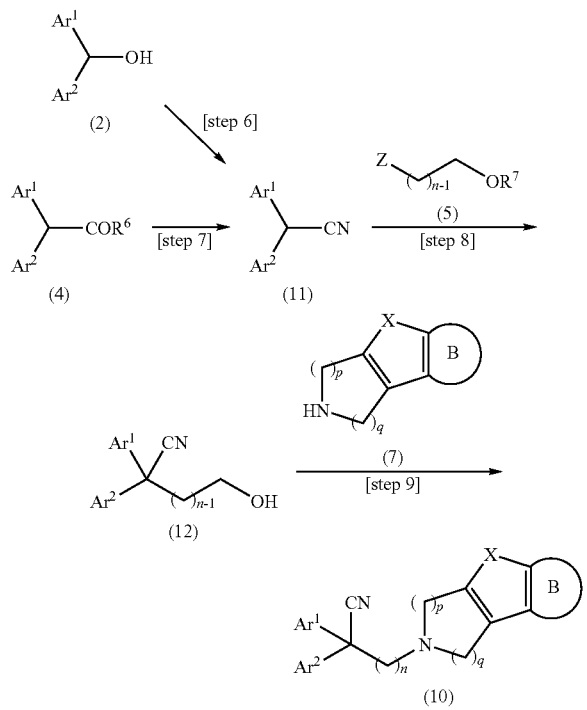

(Step 6)

Step 6 is a step to carry out a condensation reaction between compound (2) and a metal cyamide (such of sodium cyamide, potassium cyamide or copper cyamide) to thereby obtain compound (11).

The condensation reaction in step 6 may be performed, for example, by a method in which compound (2) is reacted with a halogenating reagent or sulfonylating agent in an inert solvent in the presence or absence of a base to thereby convert the hydroxyl group into an appropriate leaving group, and then a condensation reaction is carried out in an inert solvent in the presence or absence of a base. If necessary, sodium bromide, potassium iodide, or the like may be added to the reaction.

When a halogenating agent is used in step 6, examples thereof include thionyl chloride, thionyl bromide, phosphoryl chloride, phosphorus pentachloride and carbon tetrabromide-triphenylphosphine.

When a sulfonylating agent is used in step 6, examples thereof include methanesulfonyl chloride, benzenesulfonyl chloride, trifluoromethanesulfonic anhydride and N-phenyl-bis(trifluoromethanesulfonimide).

When a base is used in step 6, examples thereof include organic amines such as pyridine, triethylamine or diisopropylethylamine; and inorganic bases such as potassium carbonate, sodium hydrogencarbonate or sodium hydroxide.

Example of the inert solvent used in step 6 include alcohols such as methanol, ethanol or isopropanol; ethers such as diethyl ether, tetrahydrofuran or 1,4-dioxane; aromatic hydrocarbons such as toluene or benzene; halogenated hydrocarbons such as chloroform or dichloromethane; amides such as dimethylformamide or N-methyl-2-pyrrolidon; dimethyl sulfoxide; acetonitrile; water and a mixture thereof.

(Step 7)

Step 7 is a step to convert compound (4) wherein $R^6=NH_2$ into compound (11). In this step, the same conditions as described for step 5 in reaction scheme 2 may be used.

(Step 8)

Step 8 is a step to convert compound (11) to compound (12). In this step, the same conditions as described for step 3 in reaction scheme 1 (e.g., conditions disclosed in J. Med. Chem., 1985, 1621-1628) may be used.

(Step 9)

Step 9 is a step to obtain compound (10) of the invention by reacting compound (12) with compound (7). In this step, the same conditions as described for step 4 in reaction scheme 1 may be used.

(Reaction Scheme 4)

Hereinbelow, a method for producing the compound of the invention as shown in the following reaction scheme 4 will be described. This production process is a process for producing compound (13) of the invention from compound (8).

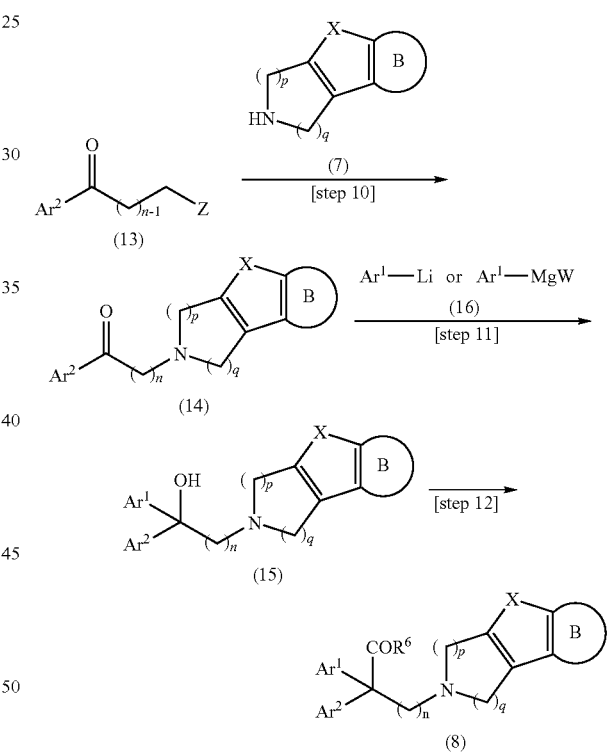

(Step 10)

Step 10 is a step to obtain compound (14) by reacting compound (13) with compound (7) in an inert solvent in the presence or absence of a base. Compound (13) is a known compound or a compound which can be easily synthesized from a known compound.

When a base is used in step 10, examples thereof include organic amines such as pyridine, triethylamine or diisopropylethylamine; and inorganic bases such as potassium carbonate, sodium hydrogencarbonate or sodium hydroxide.

Examples of the inert solvent used in step 10 include alcohols such as methanol, ethanol or isopropanol; ethers such as diethyl ether, tetrahydrofuran or 1,4-dioxane; aromatic hydrocarbons such as toluene or benzene; halogenated hydrocarbons such as chloroform or dichloromethane; amides such as dimethylformamide or N-methyl-2-pyrrolidon; dimethyl sulfoxide; acetonitrile; water and a mixture thereof (Step 11)

Step 11 is a step to obtain compound (15) of the invention by reacting compound (14) with a lithium reagent or Grignard reagent (16) in an inert solvent.

Examples of the inert solvent used in step 10 include alcohols such as methanol, ethanol or isopropanol; ethers such as diethyl ether, tetrahydrofuran or 1,4-dioxane; aromatic hydrocarbons such as toluene or benzene; halogenated hydrocarbons such as chloroform or dichloromethane; amides such as dimethylformamide or N-methyl-2-pyrrolidon; dimethyl sulfoxide; acetonitrile; water and a mixture thereof.

When a lithium reagent is used in step 11, the reagent is represented by a formula $Ar^1$—Li (wherein $Ar^1$ is as defined previously). Specific examples of the lithium reagent include phenyllithium, 4-fluorophenyllithium, 3-fluorophenyllithium, 2-fluorophenyllithium, 4-methylphenyllithium, 3,4-dichlorophenyllithium, 4-methoxynaphthyllithium and 4-pyridyllithium.

When a Grignard reagent is used in step 11, the reagent is represented by a formula $Ar^1$—MgW (wherein $Ar^1$ is as defined previously; and W is a chlorine, bromine or iodine atom). Specific examples of the Grignard reagent include phenylmagnesium bromide, 4-fluorophenylmagnesium bromide, 3-fluorophenylmagnesium chloride, 2-fluorophenylmagnesium iodide, 4-methylphenylmagnesium bromide, 3,4-dichlorophenyhnagnesium chloride, 4-methoxynaphthylmagnesium iodide and 4-pyridylnagnesium bromide.

(Step 12)

Step 12 is a step to convert compound (15) into compound (8) of the invention. In this step, the same conditions described for steps 1 and 2 in reaction scheme 1 may be used.

(Reaction Scheme 5)

Hereinbelow, a method for producing the compound of the invention as shown in the following reaction scheme 5 will be described. This production process is a process for producing compound (17) of the invention by carrying out a condensation reaction between compound (16) and compound (7).

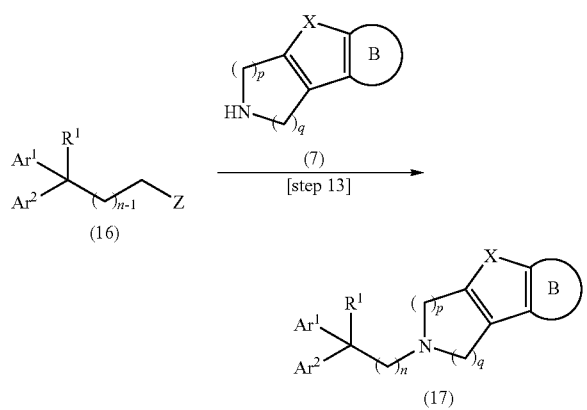

(Step 13)

Briefly, it is possible to obtain compound (17) of the invention by carrying out a condensation reaction between compound (16) and compound (7) in an inert solvent in the presence or absence of a base. Compound (16) is a known compound or a compound which can be easily synthesized from a known compound.

When a base is used in step 13, examples thereof include organic amines such as pyridine, triethylamine or diisopropylethylamine; and inorganic bases such as potassium carbonate, sodium hydrogencarbonate or sodium hydroxide.

Examples of the inert solvent used in step 13 include alcohols such as methanol, ethanol or isopropanol; ethers such as diethyl ether, tetrahydrofuran or 1,4-dioxane; aromatic hydrocarbons such as toluene or benzene; halogenated hydrocarbons such as chloroform or dichloromethane; amides such as dimethylformamide or N-methyl-2-pyrrolidon; dimethyl sulfoxide; acetonitrile; water and a mixture thereof.

In each of the above-described steps, the amounts of the compounds and solvents used in the reaction, the reaction time, the temperature and pressure of the reaction system, etc. may be selected appropriately depending on the step. Further, the compound obtained in each step may be purified by conventional purification methods such as recrystallization, reprecipitation, or purification using chromatography.

(Use of the Compound of the Invention as Medicine)

As shown in the Examples described later, the compound of the invention has a potent inhibitory effect on the binding of α2C-adrenoceptor, and shows a high selectivity for α2C/α2A subtypes in a preferred embodiment of the invention. Thus, the compound of the invention may be used effectively for preventing and treating diseases attributable to α2C-adrenoceptor (e.g., depression, anxiety and schizophrenia). More specifically, the compound of the invention may be used as a medicine such as an α2C-adrenoceptor binding inhibitor, or a prophylactic or therapeutic for the above-described diseases. The compound of the invention may be administered alone or in combination of pharmaceutically or pharmacologically acceptable carriers or diluents. When the compound of the invention is administered as the α2C-adrenoceptor binding inhibitor, or the prophylactic or therapeutic for the above-described diseases, the compound of the invention may be administered orally or parenterally without any processing. Alternatively, the compound of the invention may be administered orally or parenterally after formulation into preparations containing the compound as an active ingredient. Parenteral administration may be performed by intravenous injection.

When the above-mentioned preparations are administered orally, the compound of the invention may be administered in the form of granules, capsules, tablets, medicinal drops, troches, hard candies, powders, aerosols or the like by mixing the compound of the invention with diluents, excipients, disintegrators, binders, lubricants, antioxidants, coatings, surfactants, plasticizers, coloring agents, flavoring/aromatic agents, etc. Such preparations may be appropriately sweetened or flavored. When the above-mentioned preparations are administered parenterally, the compound of the invention may be administered in the form of injections, drips, eye drops, creams, patches, suppositories, jellies, gels, pastes, lotions, ointments, aqueous suspensions, or the like. The compound of the invention may be formulated into preparations by conventional methods.

Examples of excipients which may be used in these preparations include mannitol, xylitol, sorbitol, glucose, white sugar, lactose, crystalline cellulose, crystalline cellulose/sodium carboxymethylcellulose, calcium hydrogenphosphate, wheat starch, rice starch, corn starch, potato starch, sodium carboxymethylstarch, dextrin, α-cyclodextrin, β-cyclodextrin, carboxyvinyl polymer, light silicic anhydride, titanium oxide, magnesium aluminometasilicate, polyethylene glycol and medium chain fatty acid triglyceride.

Examples of disintegrators which may be used in these preparations include low-substituted hydroxypropylcellulose, carboxymethylcellulose, calcium carboxymethylcellulose, sodium carboxymethylcellulose, croscarmellose sodium/type A (actizol), starch, crystalline cellulose, hydroxypropyl starch and partially pregelatinized starch.

Examples of binders which may be used in these preparations include methylcellulose, hydroxypropylcellulose, hydroxypropylmethylcellulose, polyvinylpyrrolidone, gelatin, gum arabic, ethylcellulose, polyvinyl alcohol, pullulan, pregelatinized starch, agar, gum tragacanth, sodium alginate and propylene glycol alginate ester.

Examples of lubricants which may be used in these preparations include stearic acid, magnesium stearate, calcium stearate, polyoxyl stearate, cetanol, talc, hardened oil, sucrose fatty acid, dimethylpolysiloxane, microcrystalline wax, beeswax and white beeswax.

Examples of anti-oxidants which may be used in these preparations include dibutylhydroxytoluene (BHT), propyl gallate, butylhydroxyanisol (BHA), α-tocopherol and citric acid.

Examples of coatings which may be used in these preparations include hydroxypropylmethylcellulose, hydroxypropylcellulose, methylcellulose, ethylcellulose, hydroxypropylmethylcellulose phthalate, hydroxypropylmethylcellulose acetate succinate, carboxymethylethylcellulose, cellulose acetate phthalate, polyvinyl acetal diethylaminoacetate, aminoalkyl methacrylate copolymer, hydroxypropylmethylcellulose acetate succinate, methacrylate copolymer, cellulose acetate trimellitate (CAT), polyvinyl acetate phthalate and shellac.

Examples of surfactants which may be used in these preparations include polyoxyethylene hydrogenated castor oil, glycerol monostearate, sorbitan monostearate, sorbitan monopalmitate, sorbitan monolaurate, polyoxyethylene polyoxypropylene block copolymer, Polysorbates, sodium lauryl sulfate, macrogols, and sucrose fatty acid ester.

Examples of plasticizers which may be used in these preparations include triethyl citrate, triacetin and cetanol. Examples of coloring agents which may be used in these preparations include tar pigments and titanium oxide. Examples of flavoring/aromatic agents which may be used in these preparations include citric acid, adipic acid, ascorbic acid and menthol.

When the compound of the invention is administered orally, the compound may be administered 1 to 6 times a day at a dose of 1 to 2000 mg per administration, for example. When the compound of the invention is administered parenterally, the compound may be administered 1 to 6 times a day at a dose of 0.1 to 500 mg per administration, for example. The dose level of the compound of the invention may be appropriately adjusted depending on the age, body weight and symptoms of the patient to be treated.

EXAMPLES, REFERENCE EXAMPLES AND TEST EXAMPLES

Hereinbelow, the present invention will be described specifically with reference to the following Reference Examples, Examples and Test Examples. However, the present invention is not limited to these Examples.

Reference Example 1

Synthesis of bis(4-fluorophenyl)methanol

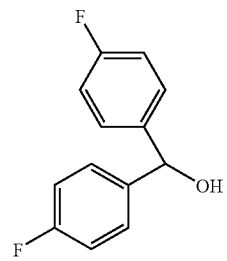

4-Fluorobromobenzene (19.26 g) in tetrahydrofuran (280 ml) was cooled to −78° C. and n-butyllithium (2.66 M n-hexane solution; 42 ml) was added thereto dropwise over 10 minutes or more while agitating. The reaction mixture was agitated for 1 hour while keeping the temperature. Then, 4-fluorobenzaldehyde (12.42 g) was added thereto dropwise over 10 minutes or more while agitating. The reaction mixture was agitated for 2 hours while keeping the temperature. Subsequently, a saturated aqueous solution of ammonium chloride was added to the reaction mixture, which was then brought to room temperature. The tetrahydrofuran was removed under reduced pressure, and the resultant residue was extracted with ethyl acetate. The organic layer washed with brine, dried with sodium sulfate, and concentrated under reduced pressure. The resultant residue was purified by silica gel column chromatography to thereby obtain the subject compound (8.28 g).

Reference Example 2

Synthesis of 2,2-bis(4-fluorophenyl)acetic acid

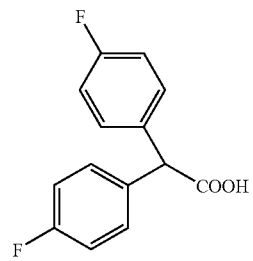

To concentrated sulfuric acid (440 ml) in ice bath, bis(4-fluorophenyl)methanol (10.97 g) obtained in Reference Example 1 was added slowly. Then, formic acid (120 ml) was added thereto dropwise over 50 minutes. Subsequently, the reaction mixture was brought to room temperature, left for 17 hours, poured into ice (5 liters) and extracted with ethyl acetate. The organic layer washed with brine, dried with sodium sulfate, and concentrated under reduced pressure.

The resultant residue was solidified with hexane to thereby obtain the subject compound (6.36 g).

Reference Example 3

Synthesis of methyl 2,2-bis(4-fluorophenyl)-5-hydroxypentanoate

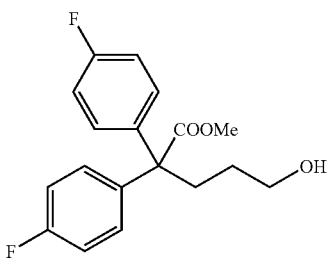

(1) Concentrated sulfuric acid (1.5 ml) was added to 2,2-bis(4-fluorophenyl)acetic acid (6.2 g; obtained in Reference Example 2) in methanol (60 ml), and the mixture was agitated for 30 minutes. This reaction mixture was poured into ice and extracted with ethyl acetate. The organic layer washed with brine, dried with sodium sulfate, concentrated under reduced pressure, and dried to thereby obtain methyl 2,2-bis(4-fluorophenyl)acetate (6.53 g).

(2) Tetrahydrofuran (3 ml) was added to sodium hydride (0.60 g) to prepare a suspension. To this suspension, methyl 2,2-bis(4-fluorophenyl)acetate (3.93 g; obtained in (1) above) in dimethyl sulfoxide (15 ml) was added dropwise at room temperature while agitating. Subsequently, 2-(3-bromopropoxy)tetrahydro-2H-pyran (3.35 g) in dimethyl sulfoxide (10 ml) was added thereto dropwise at room temperature while agitating. The resultant reaction mixture was agitated for 1 hour. A saturated aqueous solution of ammonium chloride was added to the reaction mixture, which was then extracted with ethyl acetate. The organic layer washed with brine, dried with sodium sulfate and concentrated under reduced pressure. The resultant residue was purified by silica gel column chromatography to thereby obtain methyl 2,2-bis(4-fluorophenyl)-5-(2-tetrahydropyranyloxy)pentanoate (4.45 g).

(3) Methanol (25 ml) was added to methyl 2,2-bis(4-fluorophenyl)-5-(2-tetrahydropyranyloxy)pentanoate (4.04 g) obtained in (2) above to prepare a solution, to which p-toluenesulfonic acid (0.50 g) was added, and the mixture was agitated for 3 hours. A saturated aqueous solution of sodium hydrogencarbonate (5 ml) was added to this reaction mixture, which was then concentrated under reduced pressure. Water (5 ml) was added to the resultant residue, which was then extracted with ethyl acetate. The organic layer was dried with sodium sulfate and concentrated under reduced pressure to thereby obtain the subject compound (3.05 g).

Example 1

Synthesis of Methyl 5-(3,4-dihydro[1]benzofuro[3,2-c]pyridine-2(1H)-yl)-2,2-bis(4-fluorophenyl)pentanoate (compound 1)

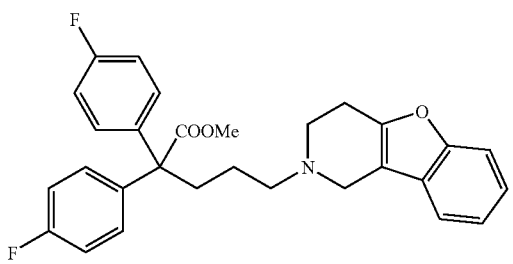

(1) Tetrahydrofuran (20 ml) was added to methyl 2,2-bis(4-fluorophenyl)-5-hydroxypentanoate (3.0 g) obtained in Reference Example 3 to prepare a solution, to which carbon tetrabromide (3.14 g) was added while agitating. The resultant mixture was agitated for 5 minutes. Then, triphenylphosphine (2.48 g) was added thereto and agitated for 30 minutes. The reaction mixture was concentrated under reduced pressure. The resultant residue was purified by silica gel column chromatography to thereby obtain methyl 2,2-bis(4-fluorophenyl)-5-bromopentanoate (2.46 g).

(2) To methyl 2,2-bis(4-fluorophenyl)-5-bromopentanoate (1.72 g) obtained in (1) above, isopropanol (7 ml), diisopropylethylamine (1.45 g) and 1,2,3,4-tetrahydrobenzo[4,5]furo[3,2-C]pyridine hydrochloride (0.94 g) were added and agitated at 110° C. for 15 hours. A saturated aqueous solution of sodium hydrogencarbonate was added to this reaction mixture, which was then extracted with ethyl acetate. The organic layer washed with brine, dried with sodium sulfate and concentrated under reduced pressure. The resultant residue was purified by silica gel column chromatography to thereby obtain the subject compound (1.77 g).

NMR of the thus obtained compound was measured. The results of measurement are as follows.

$^1$H-NMR (300 MHz, CDCl$_3$) δ 7.42-7.39 (m, 1H) 7.34-7.31 (m, 1H) 7.26-7.18 (m, 6H) 7.02-6.95 (m, 4H) 3.69 (s, 3H) 3.49 (s, 2H) 2.82-2.79 (br.s, 4H) 2.58 (t, J=7.15 Hz, 2H) 2.44-2.39 (m, 2H) 1.39-1.34 (m, 2H)

Example 2

Synthesis of 5-(3,4-dihydro[1]benzofuro[3,2-c]pyridine-2(1H)-yl)-2,2-bis(4-fluorophenylpentanoic acid (compound 2) hydrochloride

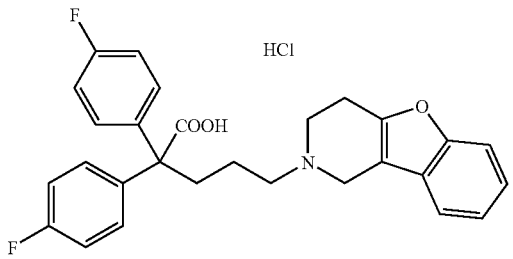

Concentrated hydrochloric acid (15 ml) was added to methyl 5-(3,4-dihydro[1]benzofuro[3,2-c]pyridine-2(1H)-yl)-2,2-bis(4-fluorophenyl)pentanoate (1.0 g) obtained in Example 1, and the resultant mixture was agitated at 150° C. for 3.5 hours. The reaction mixture was left at room temperature for cooling and concentrated under reduced pressure. The resultant residue was purified by silica gel column chromatography and dissolved in methanol (5 ml). To this solution, 4 mol/L hydrochloride ethyl acetate solution (1.5 ml) was added. The mixture was agitated and then concentrated under reduced pressure. The resultant residue was crystallized with ethyl acetate to thereby obtain the subject compound (0.18 g).

Example 3

Synthesis of 5-(3,4-dihydro[1]benzofuro[3,2-c]pyridine-2(1H)-yl)-2,2-bis(4-fluorophenyl)pentanoic acid amide (compound 3) hydrochloride

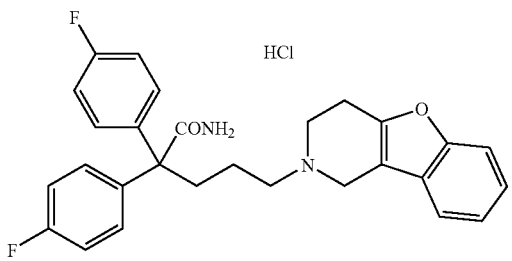

(1) Dimethylformamide (2 ml) was added to 5-(3,4-dihydro[1]benzofuro[3,2-c]pyridine-2(1H)-yl)-2,2-bis(4-fluorophenyl)pentanoic acid hydrochloride (0.3 g) obtained in Example 2 to prepare a suspension. To the resultant suspension, 1-hydroxybenzotriazole (0.15 g) and N-(3-dimethylaminopropyl)-N'-ethylcarbodiimide (0.15 g) were added. The mixture was agitated at room temperature for 15 minutes. Then, 28% aqueous ammonia was added thereto, followed by agitation for 1 hour. The reaction mixture was poured into ice water, and the deposited solid was collected by filtration. The resultant crude crystal was purified by silica gel column chromatography to thereby obtain 5-(3,4-dihydro[1]benzofuro[3,2-c]pyridine-2(1H)-yl)-2,2-bis(4-fluorophenyl)pentanoic acid amide (0.19 g).

(2) Ethyl acetate (2 ml) was added to 5-(3,4-dihydro[1]benzofuro[3,2-c]pyridine-2(1H)-yl)-2,2-bis(4-fluorophenyl)pentanoic acid amide (0.06 g) obtained in (1) above to prepare a solution. To the resultant solution, 4 mol/L hydrochloride ethyl acetate solution (0.07 ml) was added. The mixture was agitated and then concentrated under reduced pressure. The resultant residue was crystallized with diethyl ether to thereby obtain the subject compound (0.017 g).

Example 4

Synthesis of 5-(3,4-dihydro[1]benzofuro[3,2-c]pyridine-2(1H)-yl)-2,2-bis(4-fluorophenyl)pentanenitrile (compound 4) hydrochloride

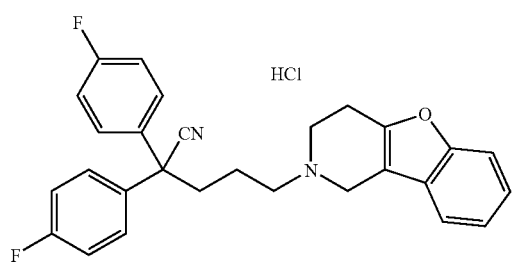

1,4-Dioxane (2.5 ml) and pyridine (0.04 g) were added to 5-(3,4-dihydro[1]benzofuro[3,2-c]pyridine-2(1H)-yl)-2,2-bis(4-fluorophenyl)pentanoic acid amide (0.1 g) obtained in Example 3. The mixture was cooled to 0° C. in ice bath, and trifluoroacetic anhydride (0.05 g) was added thereto dropwise while agitating. Then, the mixture was brought to room temperature over 30 minutes and agitated for 15 minutes. This reaction mixture was poured into ice water and extracted with chloroform. The organic layer washed with brine, dried with sodium sulfate and concentrated under reduced pressure. The resultant residue was purified by silica gel column chromatography and dissolved in ethyl acetate (3 ml) to prepare a solution. 4 mol/L hydrochloride ethyl acetate solution (0.1 ml) was added to the solution, which was then agitated and concentrated under reduced pressure. The resultant residue was crystallized with diethyl ether to thereby obtain the subject compound (0.134 g).

Example 5

Synthesis of 5-(3,4-dihydro[1]benzofuro[3,2-c]pyridine-2(1H)-yl)-2,2-diphenylpentanenitrile (compound 5) hydrochloride

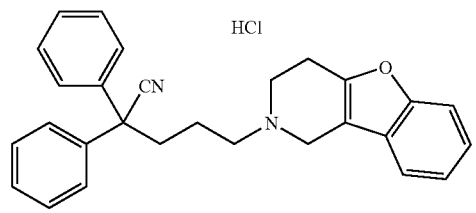

5-Bromo-2,2-diphenylpentanenitrile (1.08 g) and 1,2,3,4-tetrahydrobenzo[4,5]furo[3,2-C]pyridine hydrochloride (0.72 g) were suspended in methanol (1.72 ml). Diisopropylethylamine (1.11 g) was added to the suspension, which was then heat-refluxed for 40 hours while agitating. The reaction mixture was concentrated under reduced pressure. The resultant residue was purified by silica gel chromatography and dissolved in ethanol (5 ml) to prepare a solution. 4 mol/L hydrochloride ethyl acetate solution (0.73 ml) was added to the solution, which was then agitated and concentrated under reduced pressure. The resultant residue was crystallized with ethanol (4 ml) to thereby obtain the subject compound (0.85 g).

Examples 6-18

Compounds 6 to 18 or salts thereof (see Table 1 below) were obtained in the same manner as described in Example 5. Specifically, the following compounds were synthesized.

Compound 6:
5-(3,4-dihydro-[1]-benzofuro[2,3-C]pyridine-2(1H)-yl)-2,2-diphenyl-pentanenitrile;

Compound 7:
5-(3,4-dihydro-[1]-benzothieno[3,2-C]pyridine-2(1H)-yl)-2,2-diphenyl-pentanenitrile (hydrochloride);

Compound 8:
2,2-diphenyl-5-(1,3,4,5-tetrahydro-2H-pyrido[4,3-b]indole-2-yl)-pentanenitrile (hydrochloride);

Compound 9:
5-(5-methyl-1,3,4,5-tetrahydro-2H-pyrido[4,3-b]indole-2-yl)-2,2-diphenyl-pentanenitrile (hydrochloride);

Compound 10:
5-(8-fluoro-3,4-dihydro-[1]-benzofuro[3,2-C]pyridine-2(1H)-yl)-2,2-diphenyl-pentanenitrile;

Compound 11:
5-(8-chloro-3,4-dihydro-[1]-benzofuro[3,2-C]pyridine-2(1H)-yl)-2,2-diphenyl-pentanenitrile (hydrochloride);

Compound 12:
5-(8-methyl-3,4-dihydro-[1]-benzofuro[3,2-C]pyridine-2(1H)-yl)-2,2-diphenyl-pentanenitrile (hydrochloride);

Compound 13:
5-(8-methoxy-3,4-dihydro-[1]-benzofuro[3,2-C]pyridine-2(1H)-yl)-2,2-diphenyl-pentanenitrile (hydrochloride);

Compound 14:
2,2-diphenyl-5-(8-trifluoromethoxy-3,4-dihydro-[1]-benzofuro[3,2-C]pyridine-2(1H)-yl)-pentanenitrile (hydrochloride);

Compound 15:
2-(4,4-diphenylbutyl)-1,2,3,4-tetrahydro-[1]-benzofuro[3,2-C]pyridine (hydrochloride);

Compound 16:
9-[3-(3,4-dihydro-[1]-benzofuro[3,2-C]pyridine-2(1H)-yl)-propyl]-9H-xanthene-carbonitrile (hydrochloride);

Compound 17:
4-(3,4-dihydro-[1]-benzofuro[3,2-C]pyridine-2(1H)-yl)-2,2-diphenyl-butyronitrile;

Compound 18:
6-(3,4-dihydro-[1]-benzofuro[3,2-C]pyridine-2(1H)-yl)-2,2-diphenyl-hexanenitrile.

The structures, physical properties, etc. of the compounds obtained in individual Examples are shown in Table 1 below

TABLE 1

| Compound | Example | Chemical Structure | salt | MS (ESI) | M.P. (° C.) | Solvent |
|---|---|---|---|---|---|---|
| 1 | 1 | 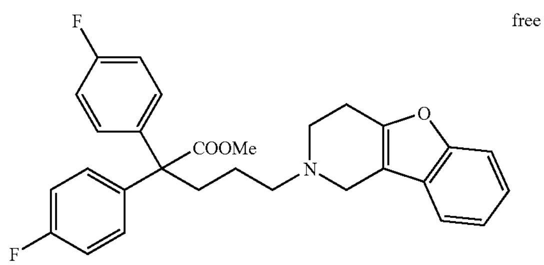 | free | 476 [M + H]+<br>498 (M + Na]− | | (oil) |
| 2 | 2 | 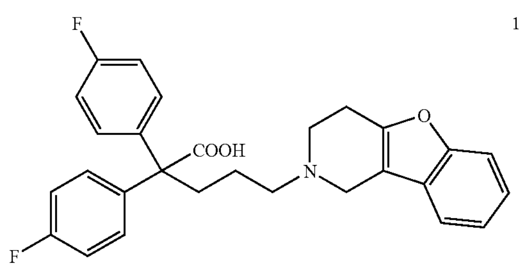 | 1 HCl | 462 (M(free) + H]+<br>484 [M(free) + Na]+ | 206.5-<br>203.0 | AcOEt |
| 3 | 3 | 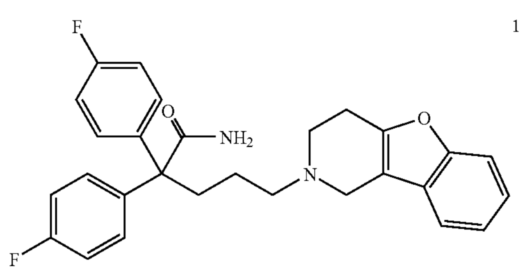 | 1 HCl | 461 [M(free) + H]+<br>483 [M(free) + Na]+ | 174.0-<br>179.5 | Et$_2$O |

TABLE 1-continued

| Compound | Example | Chemical Structure | salt | MS (ESI) | M.P. (° C.) | Solvent |
|---|---|---|---|---|---|---|
| 4 | 4 | 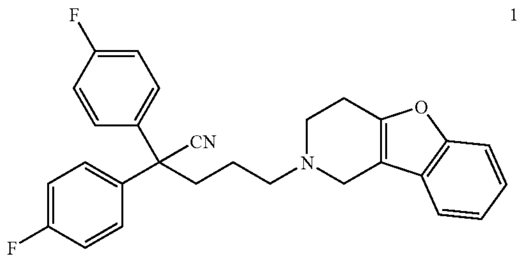 | 1 HCl | 443 [M(free) + H]$^+$<br>465 [M(free) + Na]$^-$ | 113.5-120.5 | Et$_2$O |
| 5 | 5 | 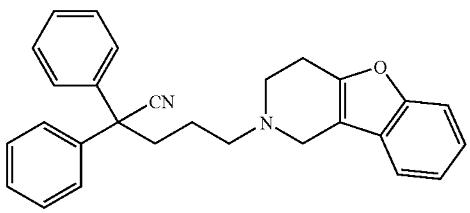 | 1 HCl | 467 [M(free) + H]$^+$<br>429 [M(free) + Na]$^-$ | 195.0-199.0 | Et$_2$OH |
| 6 | 5 | 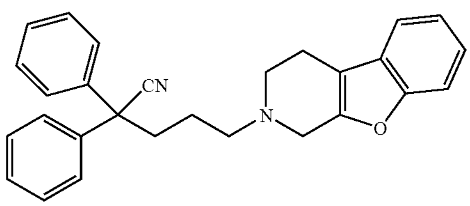 | free | 407 [M + H]$^+$<br>429 [M + Na]$^+$ | 146.0-147.0 | AcOEt—Et$_2$O |
| 7 | 5 | 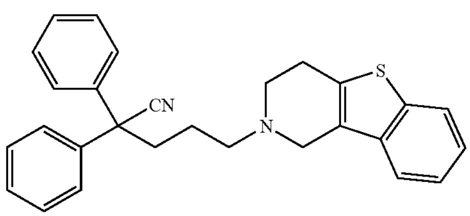 | 1 HCl | 423 [M(free) + H]$^+$<br>445 [M(free) + Na]$^-$ | 185.5-187.0 | AcOEt |
| 8 | 5 | 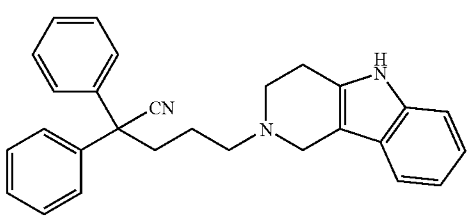 | 1 HCl | 406 [M(free) + H]$^+$<br>428 [M(free) + Na]$^+$ | 220.0-223.0 | AcOEt |
| 9 | 5 | 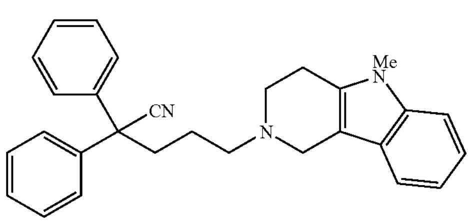 | 1 HCl | 420 [M(free) + H]$^+$<br>442 [M(free) + Na]$^+$ | 183.5-187.5 | AcOEt |

TABLE 1-continued

| Compound | Example | Chemical Structure | salt | MS (ESI) | M.P. (° C.) | Solvent |
|---|---|---|---|---|---|---|
| 10 | 5 | 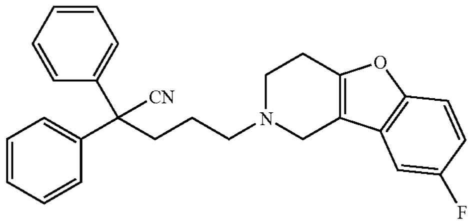 | free | 425 [M + H]+<br>441 [M + Na]+ | 128.0-<br>129.6 | Et2O |
| 11 | 5 | 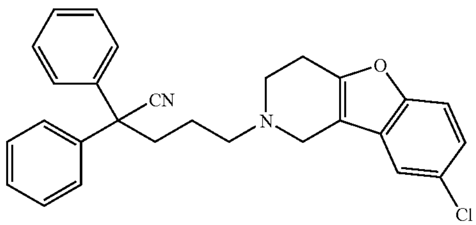 | 1 HCl | 441 [M(free) + H]+<br>463 [M(free) + Na]+ | 169.0-<br>170.5 | AcOEt |
| 12 | 5 | 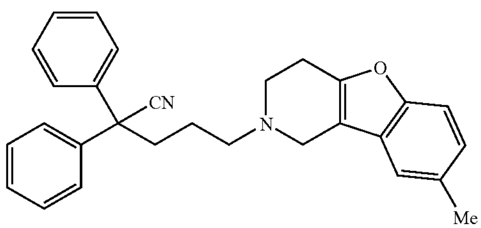 | 1 HCl | 421 [M(free) + H]−<br>443 [M(free) + Na]− | 139.0-<br>141.0 | AcOEt |
| 13 | 5 | 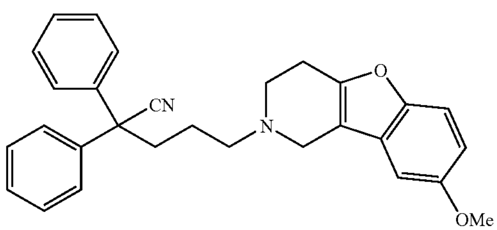 | 1 HCl | 437 [M(free) + H]+<br>459 [M(free) + Na]− | 211.0-<br>212.0 | AcOEt |
| 14 | 5 | 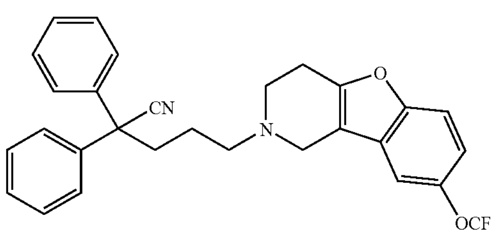 | 1 HCl | 491 [M(free) + H]+<br>513 [M(free) + Na]+ | 172.0-<br>173.0 | Et2O |
| 15 | 5 | 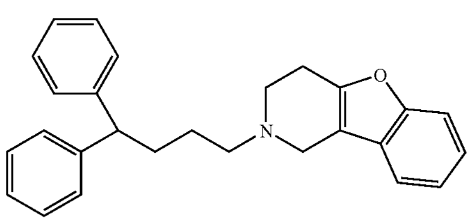 | 1 HCl | 382 [M(free) + H]+ | 164.0-<br>166.0 | AcOEt |

TABLE 1-continued

| Compound | Example | Chemical Structure | salt | MS (ESI) | M.P. (° C.) | Solvent |
|---|---|---|---|---|---|---|
| 16 | 5 | 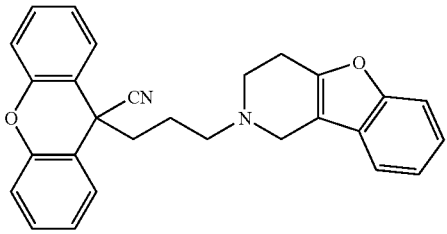 | 1 HCl | 421 [M(free) + H]$^+$ | 273 (dec.) | AcOEt |
| 17 | 5 | 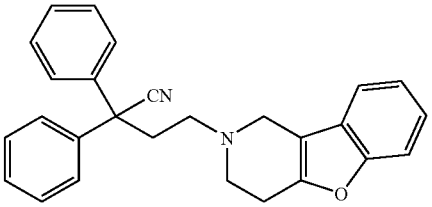 | free | 393 [M + H]$^+$<br>415 [M + Na]$^+$ | 160.5-163.5 | Et$_2$O |
| 18 | 5 | 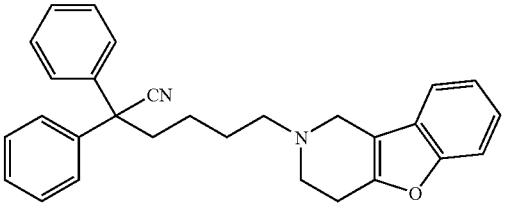 | free | 421 [M + H]$^+$<br>443 [M + Na]$^+$ | 130.5-133.5 | Et$_2$O |

Test Example 1

α2-Adrenoceptor Binding Experiment (1) α2C-Adrenoceptor Binding Experiment

The subject experiment was performed by a method improved from the method described in Uhlen et al., Journal of Pharmacology and Experimental Therapeutics (1994), 1558-1565. Briefly, human α2C-adrenoceptor expressing COS-1 cells were homogenized with 50 mM Tris-HCl buffer (pH 7.4) containing 12.5 mM magnesium hydrochloride and 1 mM EDTA. The resultant homogenate was centrifuged at 48,000×g for 20 minutes at 4° C. twice. The precipitate was suspended in 50 mM Tris-HCl buffer (pH 7.4) containing 12.5 mM magnesium hydrochloride and 1 mM EDTA to give a protein concentration of 150 μg/ml. This suspension was used in binding experiments as a crude membrane sample. The crude membrane sample (0.5 ml, 75 μg protein) was reacted with [$^3$H] MK912 (final concentration 0.08 nM) at 25° C. for 60 minutes. After completion of the reaction, the reaction mixture was vacuum filtered on GF/B glass fiber filter pre-immersed in 0.3% polyethyleneimine for 2 hours, using a cell harvester for binding experiments. The filter was placed in a glass vial containing 8 ml of Aquasol 2, and the radioactivity thereof was measured with a liquid scintillation counter. The amount of binding in the presence of 10 μM rauwolcine was taken as non-specific binding. The value obtained by subtracting non-specific binding from the total binding in the absence of 10 μM rauwolcine was taken as specific binding. Each of the test compounds was dissolved in 100% dimethyl sulfoxide solution and added to the membrane sample simultaneously with [$^3$H] MK912. IC$_{50}$ values were calculated from inhibition curves at concentrations from 0.1 nM to 1 μM. The results are shown in Table 2 below.

(2) α2A-Adrenoceptor Binding Experiment

The subject experiment was performed by a method improved from the method described in Uhlen et al., Journal of Pharmacology and Experimental Therapeutics (1994), 1558-1565. Briefly, human α2A-adrenoceptor expressing COS-7 cells were homogenized with 50 mM Tris-HCl buffer (pH 7.4) containing 12.5 mM magnesium hydrochloride and 1 mM EDTA. The resultant homogenate was centrifuged at 48,000×g for 20 minutes at 4° C. twice. The precipitate was suspended in 50 mM Tris-HCl buffer (pH 7.4) containing 12.5 mM magnesium hydrochloride and 1 mM EDTA to give a protein concentration of 200 μg/ml. This suspension was used in binding experiments as a crude membrane sample. The crude membrane sample (0.1 ml, 20 μg protein, reaction volume 0.2 ml) was reacted with [$^3$H] MK912 (final concentration 1 nM) at 25° C. for 60 minutes. After completion of the reaction, the reaction mixture was vacuum filtered on GF/C glass fiber plate pre-immersed in 0.3% polyethyleneimine for 2 hours, using a Filtermate Harvester. Microscinti-0 (40 μl) was added to the plate, and the radioactivity was measured with Top Count (PerkinElmer). The amount of binding in the presence of 10 μM rauwolcine was taken as non-specific binding. The value obtained by subtracting non-specific binding from the total binding in the absence of 10 μM rauwolcine was taken as specific binding. Each of the test compounds was dissolved in 100% DMSO solution and added to the membrane sample simultaneously with [$^3$H] MK912. IC$_{50}$ values were calculated from inhibition curves at concentrations from 1 nM to 10 μM. The results are shown in Table 2 below.

TABLE 2

| Compound | Chemical Structure | Ability to Inhibit(IC$_{50}$,nM) α 2C | α 2A |
|---|---|---|---|
| 1 | 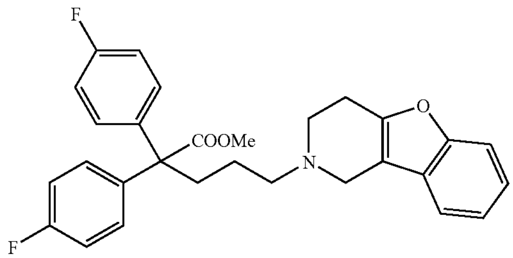 | 28 | 416 |
| 2 | 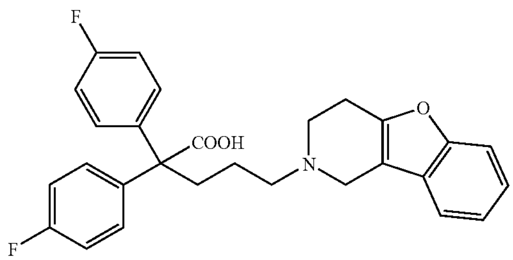 | 142 | 935 |
| 3 | 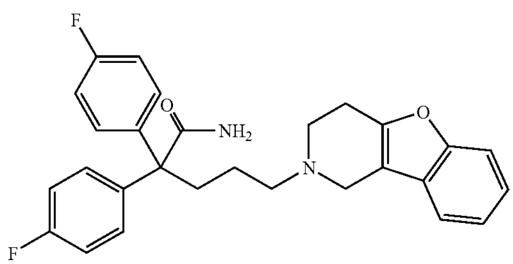 | 5.8 | 204 |
| 4 | 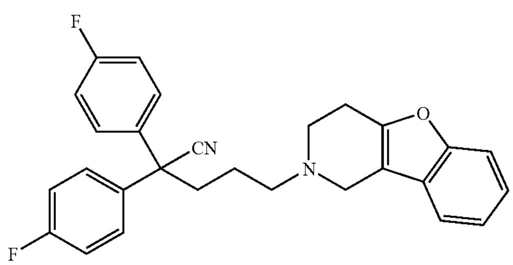 | 9.3 | 136 |
| 5 | 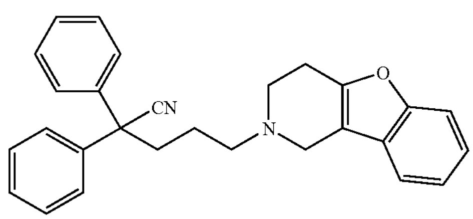 | 5.7 | 139 |
| 7 | 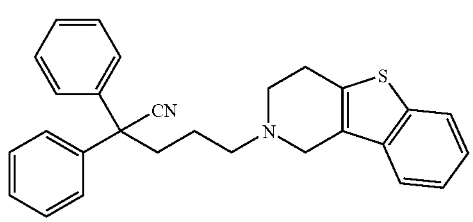 | 299 | 1483 |

TABLE 2-continued
| Compound | Chemical Structure | Ability to Inhibit(IC$_{50}$,nM) α 2C | α 2A |
|---|---|---|---|
| 8 | 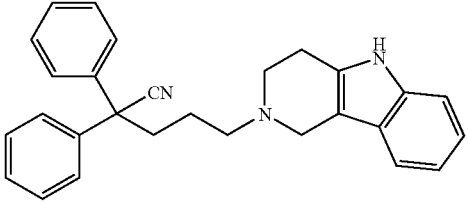 | 121 | 1292 |
| 9 | 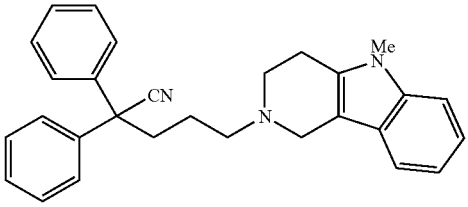 | 280 | 4827 |
| 10 | 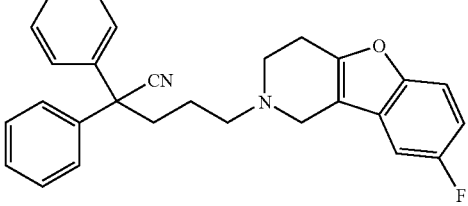 | 28 | 504 |
| 11 | 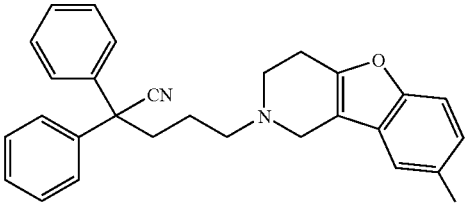 | 203 | 1719 |
| 13 | 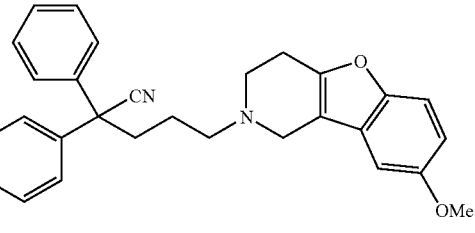 | 53 | 563 |
| 15 | 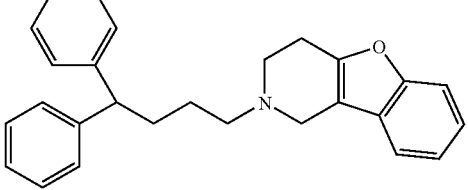 | 10 | 243 |

TABLE 2-continued

| Compound | Chemical Structure | Ability to Inhibit($IC_{50}$,nM) α 2C | α 2A |
|---|---|---|---|
| 16 | 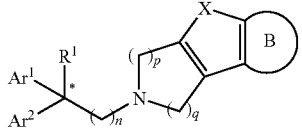 | 12 | 102 |

As shown in Tables 1 and 2, the compound of the invention has a highly selective inhibitory effect against the binding of α2C-adrenoceptor.

INDUSTRIAL APPLICABILITY

The compound of the invention is chemically and pharmacologically applicable as a novel cyclic amine compound, a solvate thereof or a pharmaceutically acceptable salt thereof.

Since the compound of the invention has inhibitory effect especially against the binding of α2C-adrenoceptor, the compound may be effectively used as a prophylactic or therapeutic for disorders attributable to α2C-adrenoceptor, e.g., depression, anxiety or schizophrenia.

What is claimed is:

1. A cyclic amine compound represented by the following formula (I) or a pharmaceutically acceptable salt thereof Formula (1)

wherein X is O, S, or $NR^2$ (wherein $R^2$ is a hydrogen atom, a $C_1$-$C_{12}$ alkyl group, a $C_2$-$C_8$ alkanoyl group or a $C_2$-$C_{13}$ alkoxycarbonyl group);

$R^1$ is, when X is O or S, a hydrogen atom, a cyano group, a carboxyl group, a $C_2$-$C_{13}$ alkoxycarbonyl group, a carbamoyl group, a $C_2$-$C_{13}$ alkylaminocarbonyl group, a $C_3$-$C_{25}$ dialkylaminocarbonyl group, a $C_3$-$C_{13}$ cyclic aminocarbonyl group, a $C_1$-$C_{12}$ alkyl group, a $C_1$-$C_{12}$ alkoxy group, a $C_1$-$C_8$ alkylthio group, a $C_1$-$C_8$ alkylsulfinyl group, a $C_1$-$C_8$ alkylsulfonyl group, a $C_2$-$C_8$ alkanoyl group, a nitro group or a hydroxyl group; and when X is $NR^2$ (wherein $R^2$ is as defined above), $R^1$ is a cyano group, a carboxyl group, a $C_2$-$C_{13}$ alkoxycarbonyl group, a carbamoyl group, a $C_2$-$C_{13}$ alkylaminocarbonyl group, a $C_3$-$C_{25}$ dialkylaminocarbonyl group, a $C_3$-$C_{13}$ cyclic aminocarbonyl group, a $C_1$-$C_{12}$ alkyl group, a $C_1$-$C_{12}$ alkoxy group, a alkylthio group, a $C_1$-$C_8$ alkylsulfinyl group, a $C_1$-$C_8$ alkylsulfonyl group, a $C_2$-$C_8$ alkanoyl group, a nitro group or a hydroxyl group;

$Ar^1$ and $Ar^2$ each represent a phenyl group which may be substituted by 1 to 3 substituents selected arbitrarily from the group consisting of halogen atoms, $C_1$-$C_{12}$ alkyl, $C_1$-$C_8$ haloalkyl, $C_7$-$C_{26}$ aralkyl, $C_2$-$C_8$ alkenyl, $C_2$-$C_8$ alkynyl, $C_1$-$C_{12}$ alkoxy, $C_1$-$C_8$ haloalkoxy, hydroxyl, $C_1$-$C_8$ alkylthio, $C_1$-$C_8$ alkylsulfinyl, $C_1$-$C_8$ alkylsulfonyl, $C_1$-$C_{12}$ alkylamino, $C_2$-$C_{24}$ dialkylamino, $C_2$-$C_{12}$ cyclic amino, amino, $C_2$-$C_{13}$ alkoxycarbonyl, carboxyl, $C_2$-$C_{13}$ alkylaminocarbonyl, $C_3$-$C_{25}$ dialkylaminocarbonyl, $C_3$-$C_{13}$ cyclic aminocarbonyl, carbamoyl, $C_2$-$C_8$ alkanoyl, cyano, nitro, phenyl and phenoxy groups;

ring B is a benzene ring which may be substituted by 1 to 3 substituents selected arbitrarily from the group consisting of halogen atoms, $C_1$-$C_{12}$ alkyl, $C_1$-$C_8$ haloalkyl, $C_7$-$C_{26}$ aralkyl, $C_2$-$C_8$ alkenyl, $C_2$-$C_8$ alkynyl, $C_1$-$C_{12}$ alkoxy, $C_1$-$C_8$ haloalkoxy, hydroxyl, $C_1$-$C_8$ alkylthio, $C_1$-$C_8$ alkylsulfinyl, $C_1$-$C_8$ alkylsulfonyl, $C_1$-$C_{12}$ alkylamino, $C_2$-$C_{24}$ dialkylamino, $C_2$-$C_{12}$ cyclic amino, amino, $C_2$-$C_{13}$ alkoxycarbonyl, carboxyl, $C_2$-$C_{13}$ alkylaminocarbonyl, $C_3$-$C_{25}$ dialkylaminocarbonyl, $C_3$-$C_{13}$ cyclic aminocarbonyl, carbamoyl, $C_2$-$C_8$ alkanoyl, cyano, nitro, phenyl and phenoxy groups;

n is an integer from 1 to 10; and p represents 2 and q represents 1.

2. The cyclic amine compound or pharmaceutically acceptable salt thereof according to claim 1, wherein X is O or S;

$R^1$ is a hydrogen atom, a cyano group, a carboxyl group, a $C_2$-$C_{13}$ alkoxycarbonyl group, a carbamoyl group, a $C_2$-$C_{13}$ alkylaminocarbonyl group, a $C_3$-$C_{25}$ dialkylaminocarbonyl group, a $C_3$-$C_7$ cyclic aminocarbonyl group, a nitro group or a hydroxyl group;

$Ar^1$ and $Ar^2$ each represent a phenyl group which may be substituted by 1 to 3 substituents selected arbitrarily from the group consisting of halogen atoms, $C_1$-$C_{12}$ alkyl, $C_1$-$C_8$ haloalkyl, $C_1$-$C_{12}$ alkoxy, $C_1$-$C_8$ haloalkoxy, hydroxyl, $C_1$-$C_{12}$ alkylamino, $C_2$-$C_{24}$ dialkylamino, $C_2$-$C_{12}$ cyclic amino, amino, $C_2$-$C_{13}$ alkoxycarbonyl, carboxyl, $C_2$-$C_{13}$ alkylaminocarbonyl, $C_3$-$C_{25}$ dialkylaminocarbonyl, $C_3$-$C_{13}$ cyclic aminocarbonyl, carbamoyl, cyano, nitro, phenyl and phenoxy groups;

ring B is a benzene ring which may be substituted by 1 to 3 substituents selected arbitrarily from the group consisting of halogen atoms, $C_1$-$C_{12}$ alkyl, $C_1$-$C_8$ haloalkyl, $C_1$-$C_{12}$ alkoxy, $C_1$-$C_8$ haloalkoxy, hydroxyl, $C_1$-$C_{12}$ alkylamino, $C_2$-$C_{24}$ dialkylamino, $C_2$-$C_{12}$ cyclic amino, amino, $C_2$-$C_{13}$ alkoxycarbonyl, carboxyl, $C_2$-$C_{13}$ alkylaminocarbonyl, $C_3$-$C_{25}$ dialkylaminocarbonyl, $C_3$-$C_{13}$ cyclic aminocarbonyl, carbamoyl, cyano, nitro, phenyl and phenoxy groups;

n is an integer from 1 to 5; and p represents 2 and q represents 1.

3. The cyclic amine compound or pharmaceutically acceptable salt thereof according to claim 1, wherein X is $NR^2$ (wherein $R^2$ is a hydrogen atom or a $C_1$-$C_{12}$ alkyl group);

$R^1$ is a cyano group, a carboxyl group, a $C_2$-$C_{13}$ alkoxycarbonyl group, a carbamoyl group, a $C_2$-$C_{13}$ alkylaminocarbonyl group, a $C_3$-$C_{25}$ dialkylaminocarbonyl group, a $C_3$-$C_7$ cyclic aminocarbonyl group, a nitro group or a hydroxyl group;

$Ar^1$ and $Ar^2$ each represent a phenyl group which may be substituted by 1 to 3 substituents selected arbitrarily from the group consisting of halogen atoms, $C_1$-$C_{12}$ alkyl, $C_1$-$C_8$ haloalkyl, $C_1$-$C_{12}$ alkoxy, $C_1$-$C_8$ haloalkoxy, hydroxyl, $C_1$-$C_{12}$ alkylamino, $C_2$-$C_{24}$ dialkylamino, $C_2$-$C_{12}$ cyclic amino, amino, $C_2$-$C_{13}$ alkoxycarbonyl, carboxyl, $C_2$-$C_{13}$ alkylaminocarbonyl, $C_3$-$C_{25}$ dialkylaminocarbonyl, $C_3$-$C_{13}$ cyclic aminocarbonyl, carbamoyl, cyano, nitro, phenyl and phenoxy groups;

ring B is a benzene ring which may be substituted by 1 to 3 substituents selected arbitrarily from the group consisting of halogen atoms, $C_1$-$C_{12}$ alkyl, $C_1$-$C_8$ haloalkyl, $C_1$-$C_{12}$ alkoxy, $C_1$-$C_8$ haloalkoxy, hydroxyl, $C_1$-$C_{12}$ alkylamino, $C_2$-$C_{24}$ dialkylamino, $C_2$-$C_{12}$ cyclic amino, amino, $C_2$-$C_{13}$ alkoxycarbonyl, carboxyl, $C_2$-$C_{13}$ alkylaminocarbonyl, $C_3$-$C_{25}$ dialkylaminocarbonyl, $C_3$-$C_{13}$ cyclic aminocarbonyl, carbamoyl, cyano, nitro, phenyl and phenoxy groups;

n is an integer from 1 to 5; and p represents 2 and q represents 1.

4. The cyclic amine compound or pharmaceutically acceptable salt thereof according to claim 1, wherein X is O or S;

$R^1$ is a hydrogen atom, a cyano group, a carboxyl group, a $C_1$-$C_6$ alkoxycarbonyl group or a carbamoyl group;

$Ar^1$ and $Ar^2$ each represent a phenyl group which may be substituted by halogen atom(s), $C_1$-$C_6$ alkyl group(s), $C_1$-$C_6$ alkoxy group(s), trifluoromethyl group(s) or trifluoromethoxy group(s);

ring B is a benzene ring wherein one of its hydrogen atoms may be substituted by a halogen atom, a $C_1$-$C_6$ alkyl group, a $C_1$-$C_6$ alkoxy group, a trifluoromethyl group or a trifluoromethoxy group;

n is an integer from 2 to 4; and p represents 2 and q represents 1.

5. The cyclic amine compound or pharmaceutically acceptable salt thereof according to claim 1, wherein X is $NR^2$ (wherein $R^2$ is a hydrogen atom, a methyl group or an ethyl group);

$R^1$ is a cyano group, a carboxyl group, a $C_1$-$C_6$ alkoxycarbonyl group or a carbamoyl group;

$Ar^1$ and $Ar^2$ each represent a phenyl group which may be substituted by halogen atom(s), $C_1$-$C_6$ alkyl group(s), $C_1$-$C_6$ alkoxy group(s), trifluoromethyl group(s) or trifluoromethoxy group(s);

ring B is a benzene ring wherein one of its hydrogen atoms may be substituted by a halogen atom, a $C_1$-$C_6$ alkyl group, a $C_1$-$C_6$ alkoxy group, a trifluoromethyl group or a trifluoromethoxy group;

n is an integer from 2 to 4; and p represents 2 and q represents 1.

6. An $\alpha_{2C}$-adrenoceptor binding inhibitor comprising the cyclic amine compound or pharmaceutically acceptable salt thereof according to any one of claims 1 to 5.

7. A pharmaceutical composition comprising the cyclic amine compound or pharmaceutically acceptable salt thereof according to any one of claims 1 to 5 and a pharmaceutically acceptable carrier.

8. The pharmaceutical composition according to claim 7, which is used for treating depression, anxiety or schizophrenia.

* * * * *

UNITED STATES PATENT AND TRADEMARK OFFICE
CERTIFICATE OF CORRECTION

PATENT NO.      : 7,601,734 B2                                       Page 1 of 1
APPLICATION NO. : 11/578169
DATED           : October 13, 2009
INVENTOR(S)     : Kumagai et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 171 days.

Signed and Sealed this

Fifth Day of October, 2010

David J. Kappos
*Director of the United States Patent and Trademark Office*